United States Patent [19]

Fraschini et al.

[11] Patent Number: 5,552,428
[45] Date of Patent: Sep. 3, 1996

[54] COMPOUNDS EFFECTIVE IN THE TREATMENT OF CIRCADIAN RHYTHMS AND RELATED DISORDERS, THE NOVEL PHARMACEUTICAL PREPARATIONS AND NOVEL METHOD OF APPLICATION

[75] Inventors: Franco Fraschini; Bojidar Stankov; Margherita Borgonovo; Carlo Introini; Aldo Laguzzi, all of Milan; Ermanno Duranti, deceased, late of Milan; Maria T. Moni, heir, Urbino, all of Italy

[73] Assignee: Instituto Farmacologico Lombardo-IFLO, S.a.S., Milan, Italy

[21] Appl. No.: 196,380

[22] Filed: Feb. 15, 1994

Related U.S. Application Data

[63] Continuation-in-part of Ser. No. 80,742, Jun. 22, 1993, abandoned, and Ser. No. 85,392, Jun. 30, 1993, abandoned.

[30] Foreign Application Priority Data

Jun. 24, 1992 [IT] Italy .................................. MI92A1556
Jul. 1, 1992 [IT] Italy .................................. MI92A1612

[51] Int. Cl.$^6$ .................. A61K 31/40; C07D 209/14
[52] U.S. Cl. .................................. 514/415; 548/507
[58] Field of Search ........................ 548/507; 514/415

[56] References Cited

U.S. PATENT DOCUMENTS 4,087,444  4/1978  Flaugh et al. ............................ 548/507
5,242,941  9/1993  Lewy et al. ............................. 514/416
5,264,219  11/1993  Godbey et al. ......................... 424/449
5,284,660  2/1994  Lee et al. ................................ 424/449

*Primary Examiner*—Jacqueline Haley
*Attorney, Agent, or Firm*—Bucknam and Archer

[57] ABSTRACT

The novel compounds of formula:

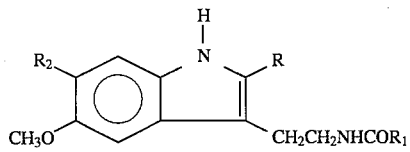

in which R is isopropyl, cyclohexyl, phenyl, $CH_3$, Br or I; or H $R_1$ is $CH_3$ or cyclopropyl and $R_2$ is H or Br, and when $R_1$ is cyclopropyl and $R_2$ is H, R is other than H, and when $R_1$ is $CH_3$ and $R_2$ is H, R is other than H, and when $R_1$ is $CH_3$ and $R_2$ is H, R is other than I, and when R is $CH_3$ and $R_2$ is H, $R_1$ is other than $CH_3$, and when R is phenyl and $R_2$ is H, $R_1$ is other than $CH_3$, exhibit superior activity in the treatment of pathologies which interfere with the circadian rhythm. A novel method of preparation is described according to which the pharmaceutical compositions containing the novel compounds, as well as compounds already known, are administered transdermally. The novel method of administration results in sustained peripheral blood level. Novel pharmaceutical compositions are described suitable for transdermal administration.

22 Claims, 5 Drawing Sheets

COMPOUNDS EFFECTIVE IN THE TREATMENT OF CIRCADIAN RHYTHMS AND RELATED DISORDERS, THE NOVEL PHARMACEUTICAL PREPARATIONS AND NOVEL METHOD OF APPLICATION

This application is a continuation-in-part of U.S. application Ser. No 08/080,742 filed Jun. 22, 1993 abandoned, and U.S. application Ser. No. 08/085,392 filed Jun. 30, 1993, abandoned.

FIELD OF THE INVENTION

The present invention relates to new pharmaceutical compounds that are effective in the treatment of circadian rhythm and related disorders, and pharmacological preparations and methods for their application.

BACKGROUND OF THE INVENTION

Under the conditions of natural environment body rhythms are adapted to the regular alternation of day and night, and the much slower monthly and seasonal cycles. The human seasonality is perceptive and indeed very important in some circumstances (Seasonal Affective Disorder, or Winter Depression) despite the almost universal use of artificial lighting and heating. Nevertheless, humans remain a diurnal species and often, the social organization leads to specific conflicts between the physiology and the environment.

Melatonin (N-acetyl-5-methoxytryptamine) is a hormone synthesized exclusively in the vertebrate pineal gland in rhythmic manner with elevated pineal, cerebrospinal fluid and peripheral blood levels at night. It has a very well expressed, high-amplitude circadian rhythm, controlled by the circadian biological clock. The phase of the rhythm is synchronized by light to the prevailing photoperiod and thus, melatonin serves as a fundamental biochemical transducer of the photoperiodic information from the environment. The most-well documented action of melatonin is its ability to drive the reproductive competence in a number of seasonal breeders, presumably acting on the endogenous biological clock. Recent research, however, pointed out at diverse sites and modes of action of melatonin, related to a synchronization necessary for the expression of other endogenous rhythms within the circadian organization. Therefore, one should expect that melatonin is involved in a number of pathological conditions, related to circadian disorganization and disease (chronopathology).

In recent years the discovery and the description of high affinity melatonin receptors in the Central Nervous System of vertebrates led to a rapid development in the field. The sites and cellular mechanism(s) of action of the indole were described, some melatonin analogues were synthesized and models for testing their activity described.

Among the possible applications of melatonin and its potent agonists in human medicine should be mentioned:

1. Circadian disorientation and disease (chronopathology).

The major applications are:

1.a. Jet- lag. Strong circadian desynchronization is observed in air travellers rapidly crossing more than five time zones, the phenomenon being more prominent when crossing Eastward. Jet-lag has been treated with melatonin, given orally with appropriate schedule [Arendt et al. Ergonomics 30, 1379–1391 (1987); U.S. Pat. Nos. 4,600,723 and 5,242,941)], but there are serious problems related to the individual absorption rates and melatonin bioavailability [Waldhauser et al., Neuroendocrinology 39, 307–313 (1984)].

1.b. Sleep disturbances, due to circadian alesynchronization, e.g. delayed sleep phase syndrome. Timed melatonin treatment produces notable phase-advances in subjects affected by delayed sleep phase syndrome, and leads to a stable improvement of the timing of sleep [Dahlitz et al., Lancet i337, 11121–1124 (1991)].

1.b.1. Disorders in the temporal, macrostrutural and microstructural organization of the sleep. Melatonin will also probably become an important supplement therapy when benzodiazepines (BDZ) are employed for the treatment of insomnia. The BDZ have notable dose-dependent side effects, provoking paradoxical repercussion on sleep, diurnal anxiety and suicidal ideations, followed by development of tolerance to the BDZ therapy. Melatonin administration in combination with low BZD doses (about two times lower than prescribed) has been able to significantly improve the sleep temporal pattern, influencing the sleep macrostructure, and mainly the microstructure, while leaving intact the sleep architecture. This allows for a substantial decrease in the BZD doses, when used to treat sleep disturbances, thus avoiding the undesirable BZD doserelated side effects.

1.c. Shift work. People working on shifts very often disrupt their circadian organization with the consequences of disturbances in sleep-activity cycles, insomnia, diurnal hypoactivity, depression. Melatonin endogenous rhythm frequently is disorganized.

1.d. Treatment of desynchronized blind people. Patients that are unable to perceive light usually suffer of disturbances related to their state of free-running circadian rhythmicity. In most of the cases synchronization of their temporal activity patterns has been achieved by timed oral melatonin treatment [Palm et at., Ann. Neurol. 29, 336–339 (1991)].

2. Aging. With the advancement in age the amplitudes of both pineal and serum melatonin decline. Therefore, a number of problems, related to old age have been attributed to pineal dysfunction, but most probably we should consider it circadian dysregulation, partially related also to altered sensitivity to light.

The major applications are:

2.a Correction of the alterations in the circadian rhythms (see above).

2.b. Sleep disturbances (see above).

2.c. Immune deficit.

The immunomodulatory properties of melatonin have been repeatedly demonstrated in the recent years, using different in vivo and in vitro models. The action of melatonin is dependent on the time of administration; therefore, one more time direct influence on the circadian organization involving oscillation patterns is evident, this time in terms of immune competence.

Melatonin, given orally in doses of 0.25–10 mg has been used successfully to treat circadian disorders due to jet-lag [Arendt et al., Ergonomics 30, 1379–1393 (1987); U.S. Pat. Nos. 4,600,723 and 5,242,941)]. Moreover, timed oral melatonin treatment apparently shifts the human circadian clock according to a phase-response curve (U.S. Pat. 5,242,941).

However, oral administration of melatonin raises the following problems: 1. High, non-physiological peripheral blood melatonin levels are achieved with dosages of 1–10 mg melatonin given orally. 2. Peripheral blood melatonin levels of abnormally short duration are achieved with 0.25–0.5 mg melatonin given orally.

In both cases there is a serious drawback: either the concentration levels achieved are too high (30–1000 times higher than the endogenous ones, when 1–10 mg melatonin is given orally), or the duration of the melatonin bioavailability in the peripheral blood is abnormally short: (one–three hours with 0.25–0.5–1 mg melatonin given orally). This is due to the very short half-life of melatonin in the blood: elimination half-life (T½)=27–30 minutes in humans. The natural, endogenous melatonin bioavailability is about six–eight hours: a direct result of a continuous synthesis and release of melatonin from the pineal gland. The duration of the melatonin signal is crucial for its sustained biological effect.

In order to obtain plasmatic levels of comparable to the endogenous melatonin peak duration, oral or parenteral application of exogenous melatonin must be in very high doses (80–100 mg/dose). A similar treatment results in excessive melatonin concentrations during the first hours (60–240 minutes after administration), followed by a rapid decrease.

Moreover, when treating circadian rhythm disorders by oral melatonin, the compound is administered during daytime; thus, high pharmacological levels of melatonin are achieved with the higher dose range at inappropriate time of the photocycle (endogenous melatonin levels are high at night).

Another problem is connected with the differences in the absorption from individual to individual. The hematic levels after oral administration of melatonin may vary from individual to individual even more that 100 times, with the same dose employed.

There is also a great need for compounds that behave as selective melatonin agonists for the different type of melatonin receptor in the hypothalamic suprachiasmatic nuclei (SCN), which is the site of the circadian biological clock. The mammalian SCN express a different melatonin receptor subtype (isoform).

SUMMARY OF THE INVENTION

One object of the present invention is to provide novel selective melatonin agonists that bind with high affinity to the melatonin receptor isoform in the circadian clock (the SCN), and express high metabolic stability in vivo.

Another object is to provide a non-invasive method of administration which allows the active compound to achieve sustained peripheral blood levels for a period of 6–8 hours.

Still another object is to provide novel pharmaceutical compositions which permit to administer the active compound in a manner which allows the active compound to achieve sustained peripheral blood levels for a period of 6–8 hours.

Still another object is to provide melatonin analogs which behave as selective melatonin agonists for the different types of melatonin receptors, in order to selectively manipulate the circadian system without affecting other systems, for instance, the reproductive system.

The novel melatonin analogs described hereinbelow have been synthesized and their biological activities have been determined. Further, we found that melatonin and its agonists may be administered in a manner which permits to achieve physiologically adequate bioavailable hematic levels for prolonged, controlled periods of time, when the administration is carried out transdermally by application of compositions which contain melatonin or its agonists in the percentage between 0.1 and 5. Experimental tests have shown that the transdermal administration of melatonin or its agonists results in sustained peripheral blood levels and may be carried out by means of oils, gels, pastes, or creams, by means of solid supports such as patches, occluded or nonoccluded gauzes.

The quantity of melatonin or its agonists which must be inserted in the basic formulation may vary between 0.1 and 5% w/w, as a function of the hematic levels which one wishes to achieve and as a function of the period of administration and the variation in the structure, affinity and metabolic stability of the agonists.

The compounds described hereinbelow which are analogs of melatonin are listed hereinbelow in Table A and have the following formula:

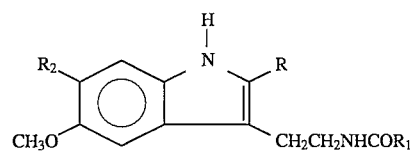

TABLE A

| Compound No. | R | $R_1$ | $R_2$ |
|---|---|---|---|
| 4a | $CH_3$ | $CH_3$ | H |
| 4b | isopropyl | $CH_3$ | H |
| 4c | cyclohexyl | $CH_3$ | H |
| 4d | phenyl | $CH_3$ | H |
| 4e | $CH_3$ | cyclopropyl | H |
| 4f | isopropyl | cyclopropyl | H |
| 4g | phenyl | cyclopropyl | H |
| 4h | Br | cyclopropyl | H |
| 4j | H | cyclopropyl | H |
| 4k | Br | $CH_3$ | H |
| 4l | Br | $CH_3$ | Br |
| 4m | I | cyclopropyl | H |
| melatonin | H | $CH_3$ | H |
| 6-Cl-melatonin | H | $CH_3$ | Cl |
| 2-I-melatonin | I | $CH_3$ | H |

BRIEF DESCRIPTION OF THE DRAWINGS

The invention is further illustrated by the accompanying figures, of which:

FIGS. 1A shows the effects of an agonist (4a) and FIG. 1B represents the blocking effect of an antagonist (4d), administered prior to the agonist 4a. The horizontal hatched bar denotes the administration of compound 4a. The arrow denotes the beginning of the administration of compound 4d.

Figure 1A:
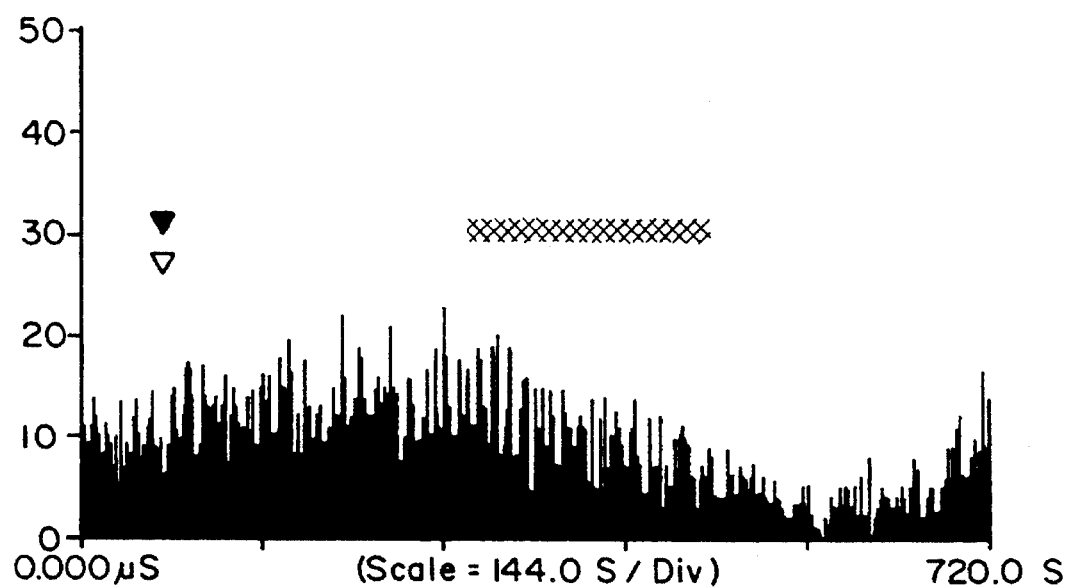
FIGS. 1A AND 1B represents recordings of the spontaneous firing activities of rabbit dorsal parietal cortex neurons. The number of spontaneous firing events is on the ordinate; time is on the abscissa.

The synthesis of the novel melatonin analogues 4a–m was achieved following the routes described in the Schemes I, II, III, IV.

The modified Madelung synthesis [Houlihan et al. J. Org. Chem 46, 4511–4515 (1981)] was adopted for the preparation of 2-substituted indoles 2a–d, starting from N-(2-methyl-5-methoxyphenyl) alkanamides or -benzamides 1a–d. The 2-substituted indoles 2a–d were coupled with 1-dimethylamino-2-nitroethylene to give the required nitrovinylindoles 3a–d in the conditions previously described for related compounds [Buchi and Mak, J. Org. Chem. 42, 1784–1786 (1977)]. The syntheses were completed by reducing the nitrovinylindoles 3a–d with lithium aluminum hydride (LiAlH$_4$) and acylating the resulting crude tryptamines with acetic anhydride or cyclopropanecarbonyl chloride in the presence of triethylamine (TEA).

Compounds 4j was obtained by acylating 5-methoxytryptamine [Yous et al., J. Med. Chem. 35, 1484–1486 (1992)] and compound 4m was obtained by acylating and 2-iodo-5-methoxytryptamine with cyclopropanecarbonyl chloride. Compounds 4h and 4k were prepared by direct bromination of 4j and melatonin, respectively, with N-bromosuccinimide. 2-Iodo-5-methoxytryptamine was synthesized as described elsewhere [Kline, Chem Abstr. 103, 876 (1985)]. Compounds 5d, and 4l were prepared by using methods, similar to those employed for related compounds [Flaugh et al., J. Med. Chem. 22, 63–67 (1979); Mistry et al., Tetrahedron Lett. 27, 1051–1054 (1986)]. Compound 5d was obtained by bromination of 5-methoxy-3-indoleacetonitrile with NBS and silica gel. Compound 4l was formed by reducing the nitrile 5d with AlH$_3$ and acylating the resulting crude tryptamine 5e with Ac$_2$O.

All new compounds were analyzed for C, H, N and the analytical results were within ±0.4% of the theoretical values. $^1$H NMR and IR data of the new compounds were found in accord with the assigned structures (see below).

The routes of preparation are illustrated by Scheme I, Scheme II, Scheme III and Scheme IV hereinbelow. Table I and Table II summarize the chemical-physical data of some of the intermediates.

SCHEME I

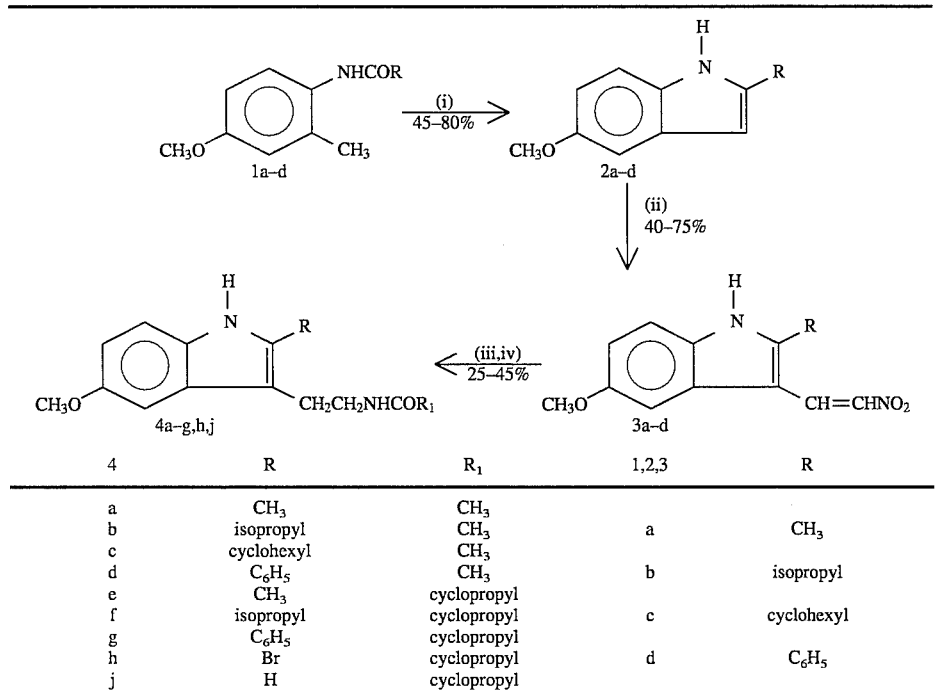

| 4 | R | R$_1$ | 1,2,3 | R |
|---|---|---|---|---|
| a | CH$_3$ | CH$_3$ | | |
| b | isopropyl | CH$_3$ | | |
| c | cyclohexyl | CH$_3$ | | |
| d | C$_6$H$_5$ | CH$_3$ | a | CH$_3$ |
| e | CH$_3$ | cyclopropyl | b | isopropyl |
| f | isopropyl | cyclopropyl | | |
| g | C$_6$H$_5$ | cyclopropyl | c | cyclohexyl |
| h | Br | cyclopropyl | | |
| j | H | cyclopropyl | d | C$_6$H$_5$ |

Reagents:
(i) n-BuLi, THF, r.t., 16 h
(ii) 1-dimethylamino-2-nitroethylene, trifluoroacetic acid, 0° C., 0.5 h
(iii) LiAlH$_4$, THF, reflux, 1 h
(iv) Ac$_2$O or cyclopropane carbonyl chloride, THF, TEA, r.t.

Scheme II

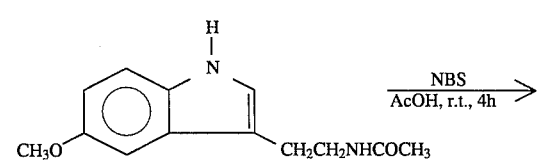

-continued
Scheme II
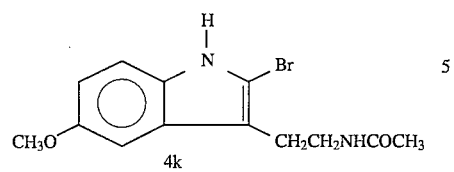
Scheme III
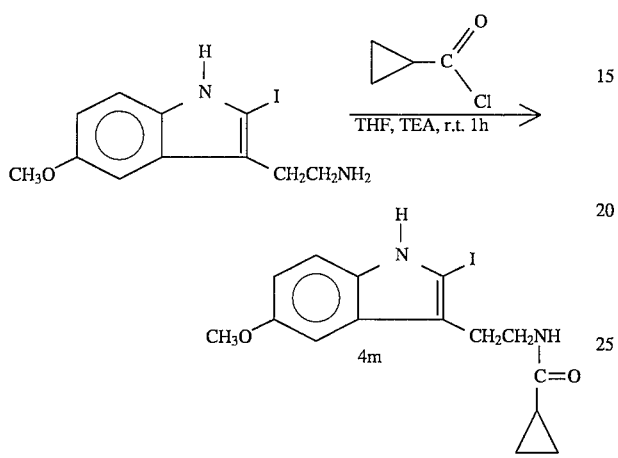
Scheme IV
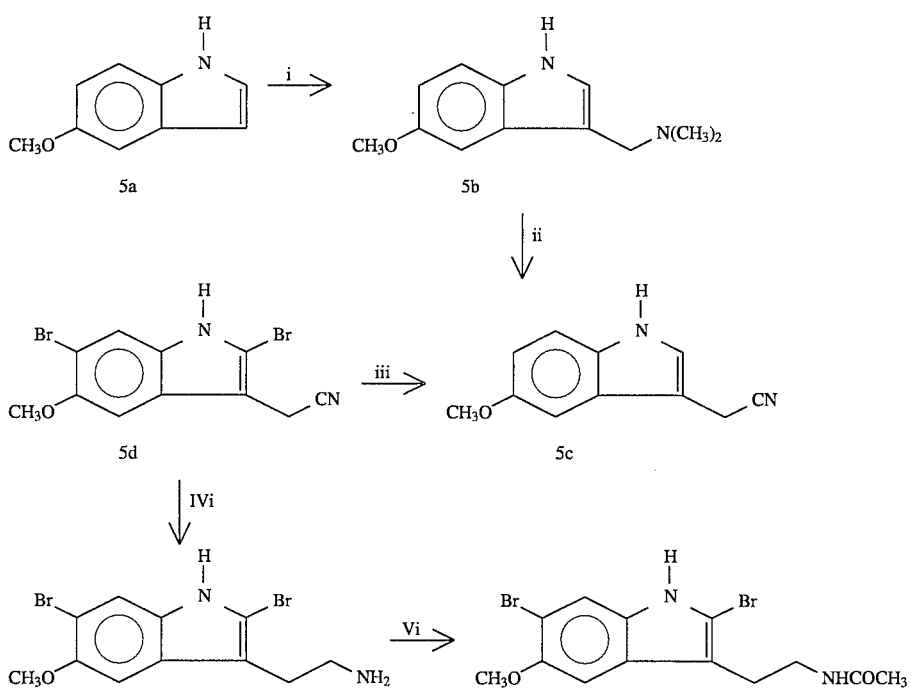
Reagents:
(i)   N,N-Dimethylmethyleneammonium iodide, CH$_2$Cl$_2$, r.t., 6h.
(i)   KCN, MeI, DFM, MeOH, H$_2$O, 50°C., 3h.
(iii)  NBS, SiO$_2$, CH$_2$Cl$_2$, R.t., 1h.
(IVi) AlH$_3$
(Vi)  Ac$_2$O, THF, TEA, r.t., 6h.

TABLE I

Chemical-Physical Data and Yields of the Amide 1c and the Indole 2c

| Compd | R | mp, °C. (solv.)[a] | Yield (%) | Formula[b] | IR (Nujol) | $^1$H NMR (CDCl$_3$) |
|---|---|---|---|---|---|---|
| 1c | cyclohexyl | 163 | 60 | $C_{15}H_{21}NO_2$ | 3280, 1640 | 1.10–1.90(complex m, 11H, Cyclohexyl), 3.35(s, 3H, CH$_3$), 3.72(s, 3H, OCH$_3$), 6.56–7.30(m, 3H$_{arom}$), 8.97(br s, 1H, NH) |
| 2c | cyclohexyl | 113–114 | 40 | $C_{15}H_{19}NO$ | 3460, 3400 1620 | 1.20–2.10(complex m, 11H, Cyclohexyl), 3.80(s, 3H, OCH$_3$), 6.10(d, 1H, H-3), 6.60–7.15(m, 3H$_{arom}$), 7.70(br s, 1H, NH) |

[a]Recrystn solvent: CH$_2$Cl$_2$/hexane
[b]All compounds analyzed for C, H, N; analitical results were within ±0.4% of theoretical values.

TABLE II

Chemical-physical Data and Yields of 2-substituted-3-(2-nitrovinyl)-5-methoxyindoles 3a–d

| Compd | R | mp, °C. | Yield (%) | Formula[a] or Lit. data | IR (Nujol) | $^1$H NMR (acetone-d$_6$) |
|---|---|---|---|---|---|---|
| 3a | CH$_3$ | 189 | 58 | 186[b] | | |
| 3b | isopropyl | 160 | 40 | $C_{14}H_{16}N_2O_3$ | 3270, 1600, 1577, 1550, 1540 | 1.40[d, 6H, CH(C$\underline{H}_3$)$_2$], 3.52[m, 1H, C$\underline{H}$(CH$_3$)$_2$], 3.88(s, 3H, OCH$_3$), 6.57–7.40(m, 3H$_{arom}$), 7.77(d, 1H, J=13Hz, =CH), 8.42(d, 1H, J=13Hz, =CH) |
| 3c | cyclohexyl | 161–162 | 60 | $C_{17}H_{20}N_2O_3$ | 3315, 1600 1565, 1550 1530 | 1.21–1.98(complex m, 11H, Cyclohexyl), 3.86(s, 3H, OCH$_3$), 6.73–7.40(m, 3H$_{arom}$), 7.66(d, 1H, J=13Hz, =CH), 8.41(d, 1H, J=13Hz, =CH) |
| 3d | phenyl | 229–232 | 75 | $C_{17}H_{14}N_2O_3$ | 3230, 1600, 1570 | 3.92(s, 3H, OCH$_3$), 6.82–7.56(m, 8H$_{arom}$), 7.86(d, 1H, J=13Hz, =CH), 8.32(d, 1H, J=13Hz, =CH) |

[a]All compounds analyzed for C, H, N; analitical results were within ±0.4% of theoretical values.
[b]Eiden, F.; Kucklaender, U. Arch. Pharm. 1971, 304(7), 523–31.

Melting points were determined on a Buchi apparatus in glass capillary tubes and are uncorrected. $^1$H NMR spectra were recorded on a Bruker 200 or a Varian EM 360 L spectrometers; chemical shifts are reported in parts per million (ppm, δ) using chloroform or tetramethylsilane as internal standards, and signals are quoted as s (singlet), d (doublet), t (triplet), q (quartet), br s (broad singlet) or m (multiplet). IR spectra were determined with a Perkin-Elmer 257 spectrophotometer; values are reported in reciprocal centimeters (cm$^{-1}$).

Satisfactory elemental analyses (±0.4%) for C, H and N were obtained using a Perkin-Elmer CHN analyzer 240C.

Tetrahydrofuran (THF) was distilled from sodium/benzophenone. Flash chromatography was carried out on Merck silica gel 60 (230–400 mesh). Compounds 1a, 2b, 1d,2d, 2b,d and 4j were prepared according to previously described procedures. The chemical physical properties of the compounds 1c and 2c are summarized in Table I. The indoles 2a, 5a and N,N-dimethylmethyleneammonium iodide are commercially available (Aldrich Chemical Co.).

General method for the synthesis of 2-substituted-3-(2-nitrovinyl)-5-methoxyindoles (3a–d).

To a stirred ice-cooled solution of 1-dimethylamino-2-nitroethylene (1.16 g, 10 mmol) in trifluoroacetic acid (6 mL) was added the appropriate 2-substituted-5-methoxyindole 2a–d (10 mmol). The mixture was stirred under N$_2$ at room temperature tier 0.5 h and then poured into ice-water. The aqueous solution was extracted with ethyl acetate; the organic phase was washed with a saturated NaHCO$_3$ solution and with water, then dried (Na$_2$SO$_4$). Evaporation of the solvent and crystallization from CH$_2$Cl$_2$/Hexane gave the required compounds 3a–d. Yields and chemical-physical data on compounds 3a–d are given in Table II.

General method for the synthesis of 2-substituted-N-acyl-5-methoxytryptamines (4a–g).

To a stirred suspension of LiAlH$_4$ (1.14 g, 30 mmol) in THF (45 mL) under a N$_2$ atmosphere was added dropwise a solution of the suitable nitrovinylindole 3a–d (5 mmol) in THF (20 mL). After the addition, the reaction was refluxed for 1 h and then allowed to stand overnight at room temperature. After cooling at 0° C., water was added dropwise to destroy the excess hydride. The mixture was filtered on celite, the tiltrate concentrated in vacuo and partitioned between water and ethyl acetate. The organic layer was washed with NaCl solution, dried (Na$_2$SO$_4$) and concentrated in vacuo to give crude tryptamines which were then used without further purification.

The syntheses of the compounds 4a–4h and 4k–4m are reported hereinbelow.

2-Methylmelatonin (4a).

To a cold solution in THF (15 mL) of the crude 2-methyl-5-methoxytryptamine, from the step above, TEA (0.7 mL) and 0.47 mL of Ac$_2$O were added. The ice bath was removed and the solution stirred for 8 h. The solvent was evaporated in vacuo, the residue was taken up in ethyl acetate and washed with a saturated aqueous solution of NaHCO$_3$ followed by saturated NaCl solution. The organic phase was dried (Na$_2$SO$_4$), concentrated under vacuum and the crude oil residue was purified by flash chromatography (silica gel; ethyl acetate-cyclohexane, 7:3) and crystallization. The overall yield of 4a was 0.541 g (44%); mp 122° C.; $^1$H NMR data were identical with that reported in literature (Flaugh et at., J. Med. Chem. 22, 63–67 (1979).

2-Isopropylmelatonin (4b).

Acetylation of the crude 2-isopropyl-5-methoxytryptamine in the above procedure gave 0.411 g (30% yield) of 4b as white amorphous solid. IR $\nu_{max}$:3450, 3300, 1655. $^1$H NMR: 1.31[d,6H,CH(C$\underline{H}_3$)$_2$], 1.92(s,3H,Ac), 2.90(t,2H,$^\beta$-CH$_2$), 3.21[m,1H, C$\underline{H}$(CH$_3$)$_2$], 3.51(q,2H,α-CH$_2$), 3.85 (s,3H,OCH$_3$), 5.65(br s,1H,NH), 6.82–7.23(m, 3H$_{arom}$), 8.06(br s ,1H,NH $_{indole}$).

2-Cyclohexylmelatonin (4c).

Acetylation of the crude 2-cyclohexyl-5-methoxytryptamine in the above procedure produced 0.660 g (42% yield) of 4c as amorphous solid. IR $\nu_{max}$: 3450, 3400, 1655. $^1$H NMR: 1.39–1.91(complex m, 11H, Cyclohexyl), 1.93(s, 3H, Ac), 2.91(t, 2H, $^\beta$-CH$_2$), 3.50(q, 2H, α-CH$_2$), 3.86(s, 3H, OCH$_3$), 5.51(br s, 1H, NH), 6.77–7.23(m, 3H$_{arom}$), 7.79(br s, 1H, NH $_{indole}$).

2-Phenylmelatonin (4d).

Acetylation of the crude 2-phenyl-5-methoxytryptamine in the above procedure afforded 0.740 g (48% yield) of 4d as amorphous solid. IR $\nu_{max}$: 3450, 3300, 1660, 1620. $^1$H NMR: 1.77(s, 3H, Ac), 3.08(t, 2H, $^\beta$-CH$_2$), 3.52(q, 2H, α-CH$_2$), 3.89(s, 3H, OCH$_3$), 5.51(br s, 1H, NH), 6.88–7.51 (m, 8H$_{arom}$), 8.25(br s, 1H, NH$_{indole}$).

2-Methyl-N-cyclopropanoyl-5-methoxytryptamine (4e).

A solution of the crude 2-methyl-5-methoxytryptamine (from 5 mmol of 3a), in THF (15 mL) and TEA (0.7 mL) was acylated with cyclopropanecarbonyl chloride (0.45 mL) at room temperature for 1.5 h using the procedure described for 4a. The desired product 4e was obtained as white solid (0.615 g, 45% overall yield), mp 102°–103° C. IR $\nu_{max}$: 3460, 3300, 1650. $^1$H NMR: 0.70(m, 2H, CH$_{2cyclopropyl}$), 0.97(m, 2H, CH$_2$ $_{cyclopropyl}$), 1.24(m, 1H, cyclopropyl-CH), 2.36(s, 3H, 2-CH$_3$), 2.90(t, 2H, $^\beta$-CH$_2$), 3.51(q, 2H, α-CH$_2$), 3.85(s, 3H, OCH$_3$), 5.75(br s, 1H, NH), 6.75–7.25 (m, 3H$_{arom}$), 8.00(br s, 1H, NH$_{indole}$).

2-Isopropyl-N-cyclopropanoyl-5-methoxytryptamine (4f).

Acylation of the crude 2-isopropyl-5-methoxytryptamine with cyclopropanecarbonyl chloride in the above procedure gave 0.375 g (25% yield) of 4f as white solid, mp 142°–143° C. IR $\nu_{max}$: 3460, 3440, 3300, 1650. $^1$H NMR: 0.69(m, 2H, CH$_{2cyclopropyl}$), 0.98(m, 2H, CH$_{2cyclopropyl}$), 1.22(m, 1H, cyclopropyl-CH), 1.33[d, 6H, CH(C$\underline{H}_3$)$_2$], 2.92(t, 2H, $^\beta$-CH$_2$), 3.23 [m, 1H, C$\underline{H}$(CH$_3$)$_2$], 3.52(q, 2H, α-CH$_2$), 3.87(s, 3H, OCH$_3$), 5.72 (br s, 1H, NH), 6.78–7.27(m, 3H$_{arom}$), 7.82(br s, 1H, NH$_{indole}$).

2-Phenyl-N-cyclopropanoyl-5-methoxytryptamine (4g).

Acylation of the crude 2-phenyl-5-methoxytryptamine with cyclopropanecarbonyl chloride in the above procedure gave 0.755 g (45% yield) of 4g as amorphous solid. IR $\nu_{max}$: 3440, 3300, 1650. $^1$H NMR: 0.66(m, 2H, CH$_{2cyclopropyl}$), 0.91(m, 2H, CH$_{2cyclopropyl}$), 1.12(m, 1H, cyclopropyl-CH), 3.10(t, 2H, $^\beta$-CH$_2$), 3.59(q, 2H, α-CH$_2$), 3.89(s, 3H, OCH$_3$), 5.69(br s, 1H, NH), 7.26–7.55 (m, 8H$_{arom}$), 8.17(br s, 1H, NH$_{indole}$).

2-Bromo-N-cyclopropanoyl-5-methoxytryptamine (4h).

N-bromo succinimide (0.89 g, 5 mmol) was added to a solution of N-cyclopropanoyl-5-methoxytryptamine, 4j (1.29 g, 5 mmol) in acetic acid (20 mL). The reaction mixture was stirred under N$_2$ at room temperature for 4 h, then cooled at 0° C., neutralized with a 50% solution of NaOH and extracted with ethyl acetate. The combined organic layers were washed with NaCl solution, dried (Na$_2$SO$_4$) and concentrated. Purification by flash chromatography (silica gel; ethyl acetate/cyclohexane 6:4) and crystallization gave 0.490 g (29% yield) of 4h as white solid, mp 82°–83° C. IR $\nu_{max}$: 3460, 3300, 1650. $^1$H NMR: 0.72(m, 2H, CH$_{2cyclopropyl}$), 0.99(m, 2H, CH$_{2cyclopropyl}$), 1.27(m, 1H, cyclopropyl-CH), 2.93(t, 2H, $^\beta$-CH$_2$), 3.56(q, 2H, α-CH$_2$), 3.85(s, 3H, OCH$_3$), 5.72(br s, 1H, NH), 6.80–7.25(m, 3H$_{arom}$), 8.21(br s, 1H, NH$_{indole}$).

2-Bromomelatonin (4k).

N-bromo succinimide (0.89 g, 5 mmol) was added to a solution of melatonin (1.16 g, 5 mmol) in acetic acid (20 mL). The reaction mixture was stirred under N$_2$ at room temperature for 4 h, then cooled at 0° C., neutralized with a 50% solution of NaOH and extracted with ethyl acetate. The combined organic layers were washed with NaCl solution, dried (Na$_2$SO$_4$) and concentrated. Purification by flash chromatography (silica gel; ethyl acetate/cyclohexane 6:4) and crystallization gave 0.467 g (30% yield) of 4k as white solid, mp 141°–142° C. IR $\nu_{max}$: 3460, 3300, 1650. $^1$H NMR: 1.99 (s, 3H, COCH$_3$); 2.92(t, 2H, $^\beta$-CH$_2$), 3.54(q, 2H, α-CH$_2$), 3.86(s, 3H, OCH$_3$), 5.53(br s, 1H, NH), 6.85–7.23(m, 3H$_{arom}$), 8.15(br s, 1H, NH$_{indole}$).

2-Iodo-N-cyclopropanoyl-5-methoxytryptamine (4m).

A solution of 2-iodo-5-methoxytryptamine (0.316 g, 1 mmol), in THF (3 mL) and TEA (0.14 mL) was acylated with cyclopropanecarbonyl chloride (0.09 mL) at room temperature for 1.5 h using the procedure described for 4a. The desired product 4m was obtained as amorphous solid (0.34 g, 89% yield), IR $\nu_{max}$:3450, 3300, 1650. $^1$H NMR: 0.71(m, 2H, CH$_{2cyclopropyl}$), 0.96(m, 2H, CH$_{2cyclopropyl}$), 1.21(m, 1H, cyclopropyl-CH), 2.90(t, 2H, $^\beta$-CH$_2$), 3.55(q, 2H, α-CH$_2$), 3.85(s, 3H, OCH$_3$), 5.62(br s, 1H, NH), 6.78–7.27(m, 3H$_{arom}$), 8.21(br s, 1H, NH$_{indole}$).

2,6-Dibromomelatonin (4l).

A solution of 5d (1.725 g, 5 mmol) in THF (10 mL) was added dropwise to a solution of AlH$_3$ (ref) (from 0.96 mL of 100% H$_2$SO$_4$ and 37 mmol of LiAlH$_4$ in 50 mL of THF). The mixture was stirred for 1 hour at room temperature, then the excess of hydride was destroyed by addition of ice. The supernatant was decanted and the aluminium salts were treated with cold 25 % NaOH, and the aqueous solution was extracted with CH$_2$Cl$_2$. The extracts were collected together with the THF solution, washed with brine, dried (Na$_2$SO$_4$) and concentrated in vacuo, to give the crude tryptamine 5e, in the form of oil.

To a cold solution of the crude 5e in THF (15 mL), TEA (0.7 mL) and 0.47 mL of Ac$_2$O were added. The ice bath was removed and the solution stirred for 8 hours. The solvent was evaporated in vacuo, the residue was taken up in ethyl acetate and washed with a saturated aqueous solution of NaHCO$_3$ followed by saturated NaCl solution. The organic phase was dried (Na$_2$SO$_4$), concentrated under vacuum and the crude oil residue was purified by flash chromatography (silica gel; ethyl acetate-cyclohexane, 7:3) and crystallization from ethyl acetate-hexane. The overall yield of 4l, starting from 5d was 0.81 g (43%); mp 146°–148° C.; IR $\nu_{max}$: 3455, 3300. $^1$H NMR: 1.97 (s, 3H, COCH$_3$); 2.91(t, 2H, $^\beta$-CH$_2$), 3.52(q, 2H, α-CH$_2$), 3.89(s, 3H, OCH$_3$), 5.58(br s, 1H, NH), 7.02 (s, 1H, H-4) 7.71(s, 1H, H-7), 8.41(br s, 1H, NH $_{indole}$).

The syntheses of the intermediate nitrile compounds 5c and 5d is reported hereinbelow.

5-Methoxy-3-indoleacetonitrile (5c).

A solution of N,N-dimethylmethylene ammonium iodide (3.25 g, 17.5 mmol) and 5-methoxyindole, 5a (1.47 g, 10 mmol) in CH$_2$Cl$_2$ (100 mL) was stirred at room temperature for 6 hours with exclusion of moisture. A saturated aqueous solution of NaHCO$_3$ was added to the ice-cooled reaction mixture with stirring. The layers were separated, the organic phase was washed with water, dried (Na$_2$SO$_4$) and evaporated in vacuo. The crude 5b was dissolved in methanol (50 mL ); 2.5 mL of DMF and 2.5 mL of water were added, followed by KCN (5.2 g, 80 mmol) and MeI (14.2 g, 100 mmol). The reaction mixture was warmed at 50° C. for 3 hours, then it was poured into ice-water and extracted with $CH_2Cl_2$. The extracts were washed with brine, dried ($Na_2SO_4$) and concentrated in vacuo. The residue was re-crystalized from ethyl acetate-hexane (1.02 g, yield: 55%, starting from 5a), oil. $^1H$ NMR: 3.71(s, 2H, $CH_2$), 3.88(s, 3H, $OCH_3$), 6.97–7.73(m, $4H_{arom}$), 8.41(br s, 1H, $NH_{indole}$).

2,6-Dibromo-5-Methoxy-3-indoleacetonitrile (5d).

Dichloromethane (10 mL), silica (3.76 g, BDH chromatography grade, 60–120 BSS mesh), 5c (0.93 g, 5 mmol) and NBS (1.8 g, 10 mmol) were stirred at room temperature for 1 hour, under nitrogen. The desired product was washed from the silica with methanol. The solvent was evaporated and the residue was purified by chromatography and crystallization, to give the compound 5d (0.83 g, yield 48%), mp 169°–171° C. $^1H$ NMR: 3.74(s, 2H, $CH_2$), 3.90(s, 3H, $OCH_3$), 7.01 (s, 1H, H-4) 7.68(s, 1H, H-7), 8.39(br s, 1H, $NH_{indole}$).

Structure-affinity studies.

From the performed structure-affinity studies, using melatonin receptors (see Table III) it became clear that only some of the 2- and/or 2,6-substituted-N-acyl-5-methoxytryptamines bind with high affinity to the melatonin receptor. Therefore, there were unpredictable structural requirements for the drug-receptor interaction.

The significance of this test is in the discovery that only a limited number of unpredictable structural modifications of the indole nucleus brings about new compounds that are 10–20 times more powerful than melatonin in their potential to produce a biological response. Specifically, Ki values represent the affinity constants obtained under in vitro ligand binding conditions with melatonin receptors. The smaller is the numerical value, the higher is the affinity for the receptor, i.e. the higher is the physico-chemical strength of interaction between the analog and the receptor. The equation Ki of the competing drug versus Ki of melatonin (e.g. 0.058 nM for 2-bromomelatonin divided by 1.1 nM for melatonin=0.053), shows that 2-bromomelatonin has an affinity about 20 times higher than melatonin, i.e. 1.1 nM for melatonin divided by 0.058 nM for 2-bromomelatonin=18.966 (melatonin is ≈19 times less potent than 2-bromomelatonin.)

On the contrary, indoles that lack the 5-methoxy group (e.g. 5-hydroxyindoles and indoles) express negligible affinity for the receptor.

Cyclopropyl substitution alone at the Noacyl of the lateral chain ($R_1$) resulted in a decrease of affinity (4j), and only few concomitant substitutions at $C_2$ (R) of the indole nucleus were able to counteract to a great extent the loss of the affinity: halogenation, methylation and a substitution with an aromatic ring (4e,g,h,m).

TABLE III

Primary evaluation of the competive potencies of the tested compounds ($K_i$ in nM) against $2[^{125}I]$-labeled melatonin under in vitro binding conditions with melatonin receptors, isolated from quail brains, from three to five independent determinations.

| Drug | $K_i$ (nM) | Affinity ratio to melatonin[a] |
|---|---|---|
| 5-Methoxyindoles: | | |
| 2-Methylmelatonin (4a) | 0.43 | 0.39 |
| 2-Ispropylmelatonin (4b) | 4.3 | 3.91 |
| 2-Cyclohexylmelatonin (4c) | 5.3 | 4.82 |
| 2-Phenylmelatonin (4d) | 0.057 | 0.052 |
| 2-Methyl-N-cyclopropanoyl-5-methoxytryptamine (4e) | 0.63 | 0.57 |
| 2-Isopropyl-N-cyclopropanoyl-5-methoxytryptamine (4f) | 18.8 | 17.09 |
| 2-Phenyl-N-cyclopropanoyl-5-methoxytryptamine (4g) | 0.24 | 0.22 |
| 2-Br—N-cyclopropanoyl-5-methoxytryptaqmine (4h) | 0.21 | 0.19 |
| N-cyclopropanoyl-5-methoxytryptamine (4j) | 2.2 | 2.00 |
| 2-Bromomelatonin (4k) | 0.058 | 0.053 |
| 2,6-Dibromomelatonin (4l) | 0.067 | 0.061 |
| 2-I—N-Cyclopropanoyl-5-methoxytryptamine (4m) | 0.10 | 0.091 |
| 2-Iodomelatonin | 0.021 | 0.019 |
| 6-Chloromelatonin | 2.2 | 2.00 |
| 5-methoxytryptamine | 1780 | 1618.2 |
| Melatonin | 1.1 | 1.00 |
| 5-Hydroxyindoles: | | |
| N-Acetyl-serotonin | 155 | 140.9 |
| 5-Hydroxytryptamine | >200,00 | >180,000 |
| 5-Hydroxytryptophan | >200,000 | >180,000 |
| Indoles: | | |
| Tryptamine | >200,000 | >180,000 |
| Indole | >200,000 | >180,000 |
| Indole acetic acid | >200,000 | >180,000 |
| Indomethacin | >200,000 | >180,000 |
| Indol-3yl-propanone | >200,000 | >180,000 |
| Miscellaneous compounds: | | |
| GABA | >200,000 | >180,000 |
| Dopamine | >200,000 | >180,000 |
| Taurine | >200,000 | >180,000 |
| Prazosin | >200,000 | >180,000 |

[a]$K_i$ of the competing drug s. $K_i$ of melatonin.

Biological activity evaluation.

From the chemical point of view, an analog is any compound, displaying close structural similarity to another molecule, but having unknown biological effects. Therefore a structural analog can behave in a biological system as agonist, antagonist or can have no activity at all. The extended sequences of experiments regarding the biological activity of the newly-synthesized compounds included two approaches, in situ and in vivo, commonly accepted as model systems.

Determination of the biological activity in vivo.

For the in vivo studies, the Syrian hamster gonadal regression model was employed. Briefly, male sexually mature Syrian hamsters (five per group), held under constant photoperiod conditions of 14:10 LD, lights off 20:00 h were treated with the tested compounds alone, in a dose of 200 µg/animal/day at 17:00 h, or 200 µg at 16:30 h, followed by 20 µg melatonin at 17:00 h, for six weeks. The negative controls were given equal volumes of saline; the positive controls received 200 µg or 20 µg melatonin at 16:30 and 17:00 h, respectively. At the end of the experimental period, the combined testes and seminal vesicle weights were recorded. Analogs that induced partial gonadal regression (testes and seminal vesicle weights equal to 50% or less, compared to the respective positive control) were considered weak agonists. Compounds that had no influence per se, but were able to block the effect of subsequent melatonin treatment were evaluated as antagonists.

Determination of the biological activity in situ.

The in situ electro physiological studies employed the rabbit parietal cortex as a model system, because it is rich in melatonin receptors [Stankov et al., Neurosci. Lett. 133, 68–72 (1991)] and the basic approach consisted of recording the spontaneous electrical activity of single rabbit parietal cortex neurons. Drugs were applied by iontophoresis, using seven-barreled glass electrodes and the currents polarity or the micropressure force were chosen according to the molecules' polarities. The recordings were displayed on oscilloscope and then analyzed on a computer, using electronic card and software for wave shape recognition, histogram analysis, data processing and averaging (R.C. Electronics, Computerscope, Santa Barbara, Calif.). Additionally, in separate series of experiments, saturating concentrations of GABA antagonists phaclofen and bicuculline ($1E^{-4}M$) were applied, starting before, and continuing during the drugs application, in order to block the possible effects of the compounds on the GABA-receptor complex and allow for a delineation of analogs' principal activities at the level of the melatonin receptor.

were unable to prevent the impact of melatonin, and their behavior was evaluated as weak agonistic (see Table IV). The only molecule that expressed no effect alone and did not influence the results of the 5subsequent melatonin administration was 4f. The significance of this test is that timed treatment with melatonin (at 16:30–17:00 on a 14 hours light—10 hours dark (LD 14:10) photoperiod, lights off at 20:00 h) will shift the circadian clock of the animal; will produce a change in the photoperiodic information supplied by the endogenous melatonin, and will result in simulation of "long nights", with a consequent gonadal regression (reduction in the testes and seminal vesicles weights) within six-eight weeks. Among the synthetic melatonin analogs, these expressing agonist activity can be distinguished from those that express antagonistic activity by studying their effects on the gonadal regression.

Iontophoretic administration of melatonin and its agonists inhibits the spontaneous firing activity, while pretreatment

TABLE IV

Biological activities of 2- and 2,6-substituted-5-Methoxy-N-acyltryptamines.

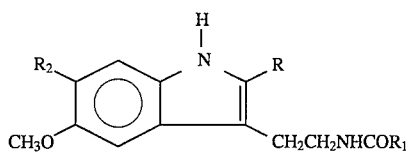

| Compound | R | $R_1$ | $R_2$ | SHGRM | RPCM | INH | LENGTH |
|---|---|---|---|---|---|---|---|
| 4a | $CH_3$ | $CH_3$ | H | Agonist | Agonist | 60 | 113 |
| 4b | isopropyl | $CH_3$ | H | Weak Agonist | Weak Agonist | 10 | 17 |
| 4c | cyclohexyl | $CH_3$ | H | Agonist | Agonist | 35 | 65 |
| 4d | phenyl | $CH_3$ | H | Antagonist | Mixed Activity* | — | — |
| 4e | $CH_3$ | cyclopropyl | H | Weak Agonist | Weak Agonist | 20 | 18 |
| 4f | isopropyl | cyclopropyl | H | No Effect | No Effect | — | — |
| 4g | phenyl | cyclopropyl | H | Antagonist | Mixed Activity** | — | — |
| 4h | Br | cyclopropyl | H | Agonist | Agonist | 60 | 200 |
| 4j | H | cyclopropyl | H | Weak Agonist | Weak Agonist | 15 | 30 |
| 4k | Br | $CH_3$ | H | Agonist | Agonist | 89 | 290 |
| 4l | Br | $CH_3$ | Br | Agonist | Agonist | 91 | 270 |
| 4m | I | cyclopropyl | H | Agonist | Agonist | 67 | 180 |
| melatonin | H | $CH_3$ | H | Agonist | Agonist | 50 | 100 |
| 6-Cl-melatonin | H | $CH_3$ | Cl | Agonist | Agonist | 46 | 96 |
| 2-I-melatonin | I | $CH_3$ | H | Agonist | Agonist | 76 | 160 |

Syrian hamster gonadal regression model;
RPCM, rabbit parietal cortex model.
INH. Per cent inhibition of the spontaneous firing activity of single cortical neurons in the RPCM, with concentrations of $1 \times 10^{-6}$ M of the tested compounds.
LENGTH, duration of the inhibitory effect in the RPCM, in comparison with melatonin, where the length of the inhibitory effect was taken as 100.
*Behaves as antagonist in 80%, and
**60% of the tested neurons, respectively.

Both experimental series confirmed that the greater part of the new compounds expressed agonist activity. Of all molecules, 4d and 4g only expressed apparent antagonist activity. The summary of the results is reported in Table IV.

Figure 1B:
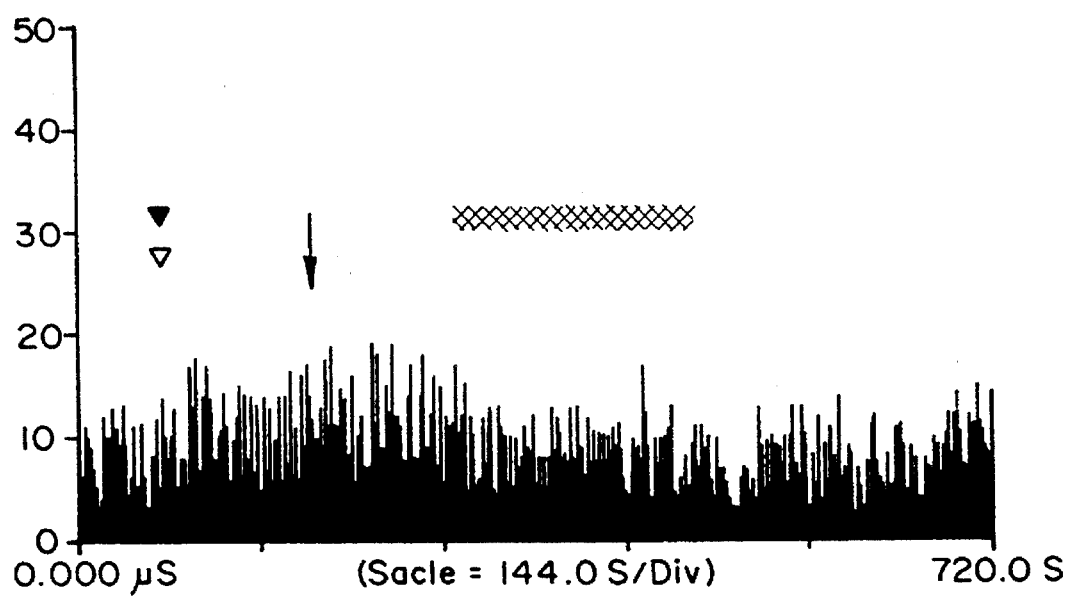

Table V shows examples of the data obtained in the Syrian hamster gonadal regression model. As clearly seen, melatonin in both doses of 20 and 200 μg/animal/day, induced complete gonadal regression within six weeks. The agonist-activity compounds generated the same response, and an excess dose of 200 μg, administered 30 minutes before melatonin (20 μg), was not able to prevent the melatonin-induced gonadal regression. On the contrary, two of the molecules tested (4d and 4g) had no effect alone in a dose of 200 μg, but efficiently prevented the aftermath of 20 μg melatonin, injected 30 minutes later. Therefore, their effect was evaluated as clearly antagonistic. Compounds 4b, 4e and 4j given alone, induced partial gonadal regression, but with an antagonist abolishes the effect of melatonin (or its agonist). The iontophoretic administration of the drugs, under conditions of the rabbit parietal cortex model were in accord with the *in vivo* data. The relative potency was determined on the basis of a large series of dose-response studies, evaluating the repercussion on the spontaneous neuronal firing rates (per cent inhibition of the spontaneous firing, and the duration of the observed effects); see Table IV, examples with $1\times10^{-6}M$ compound concentration in the electrode. Most compounds (4a, 4c, 4h, 4–4m), similarly to melatonin, expressed clearly benzodiazepine-like properties and administration of nano- to micromolar quantities always led to a significant-to-strong dose-dependent inhibition of the spontaneous firing rates of the tested cortical neurons. Therefore, their behavior was agonistic. 2-Bromomelatonin and 2,6-dibromomelatonin behaved as the strongest agonists, almost completely abolishing the spontaneous firing rate (≈90% inhibition, with a prolonged duration of their effect). The antagonistic action of 4d was most clear; 4g expressed dose-dependent mixed antagonist/weak agonist properties; 4f was without effect. A summary of the results is reported in Table IV; an example of original experimental data is given in FIG. 1. As clearly seen, iontophoretic administration of 2-methylmelatonin (4a) leads to a significant inhibition of the firing rate of the cortical neurons (FIG. 1A). Application of 4d (2-phenylmelatonin) has no significant influence per se, but is able to virtually block the effect of the subsequent administration of 4a (FIG. 1B). These structure-activity data were well in line with the results of the structure-affinity evaluation experiments.

TABLE V

Examples of the evaluation of the biological activity of the synthetic melatonin derivatives in the Syrian hamster gonadal regression model: timed melatonin treatment in the late afternoon of a LD 14:10 photoperiod induces gonadal regression within six weeks. Combined testes weights of adult male Syrian hamsters (five animal per group) trated with melatonin (20 μ/animal, s.c.) or melatonin analogs for six weeks under 14:10 LD photoperiod, lights off at 20:00h.

| Group | Time given | Testes weight (g) ± SD | | Biological evaluation |
|---|---|---|---|---|
| Saline | 17:00 h | 3.0 | 0.4 | — |
| Saline + | 16:30 h | | | |
| Mel | 17:00 h | 0.9* | 0.11 | agonist |
| Mel | 17:00 h | 1.1* | 0.15 | agonist |
| 2BM | 17:00 h | 0.65* | 0.03 | agonist |
| 2IM | 17:00 h | 0.98* | 0.08 | agonist |
| 2-Br—N-cM | 17:00 h | 0.59* | 0.02 | agonist |
| 2-I—N-cM | 17:00 h | 0.61* | 0.03 | agonist |
| 2-Ph—M | 17:00 h | 2.9 | 0.5 | ** |
| 2-Ph—M + | 16.30 h | | | |
| Mel | 17:00 | 3.1 | 0.6 | antagonist |

*$p<0.01$ vs Saline, 2-Ph—M or 2Ph—M + Mel
** 2-Ph—M was without effect alone even in a dose of 200 μg/animal, but was able to block the effect of subsequent treatment. Therefore, its behavoir was antagonistic. Note that 2-BM, 2-I—N-cM and 2-Br—N-cM induced signficantly more profound gonadal regression, given in the same doses (20 μg/animal), as melatonin ($p<0.05$), for the same oeriod of time (six weeks).
Abbreviations: Mel, melatonin; 2BM, 2-bromomelatonin; 2IM, 2-iodomelatonin; 2-Br—N-cM, 2-bromo-N-cyclopr opanoyl-5-methoxytryptamine; 2-N—cM, 2-iodo-N-cyclopropanoyl-5-methoxytryptamine, 2-PhM, 2-phenylmelatonin.

In summary, under in vivo conditions, 2-bromomelatonin, 2,6-dibromomelatonin, 2-bromo-N-cyclopropanoyl-5-methoxytryptamine and 2-iodo-N-cyclopropanoyl-5-methoxytryptamine, behaved as significantly more potent agonists than either melatonin, 6-chloromelatonin or 2-iodomelatonin.

On the basis of the structure-activity studies, few of the new compounds only (4a, 4c, 4h, 4k–m) appeared prospective melatonin agonists, i.e. those that behaved as such in both tests: Syrian hamster gonadal regression model (SHGRM), and rabbit parietal cortex model (RPCM) (see Table IV).

Figure 2A:
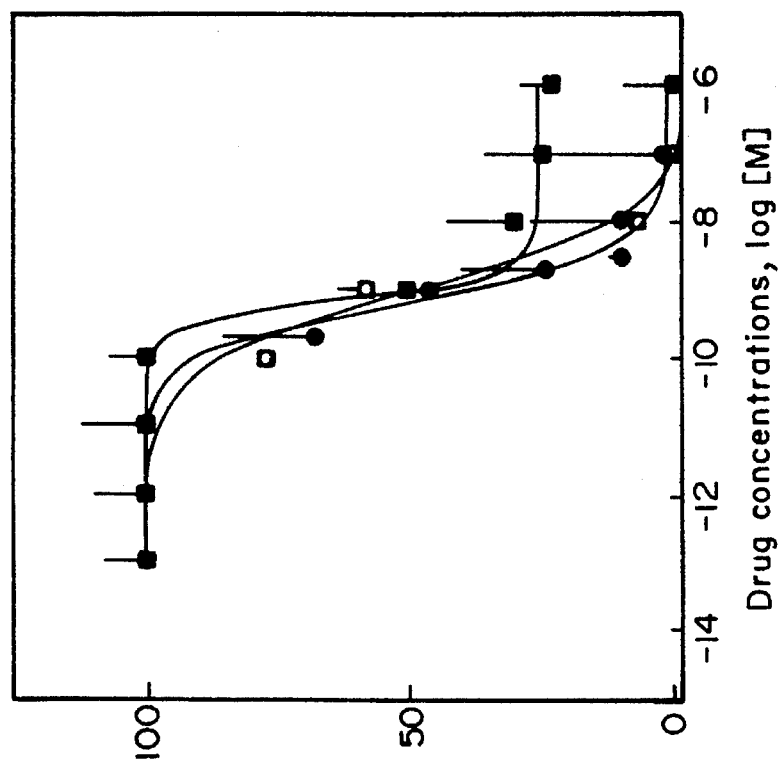
FIGS. 2A and 2B are a plot of the percent specific binding of the radioactively labeled melatonin (on the ordinate) against the increasing concentrations of 2-iodomelatonin and 2-bromo-N-cyclopropanoyl-5-methoxytryptamine (on the abscissa) in the SCN FIGS. 2A and pars tuberalis (FIG. 2B), following long- or short-time washes after incubation, under conditions of quantitative autoradiography procedure.
Figure 2B:
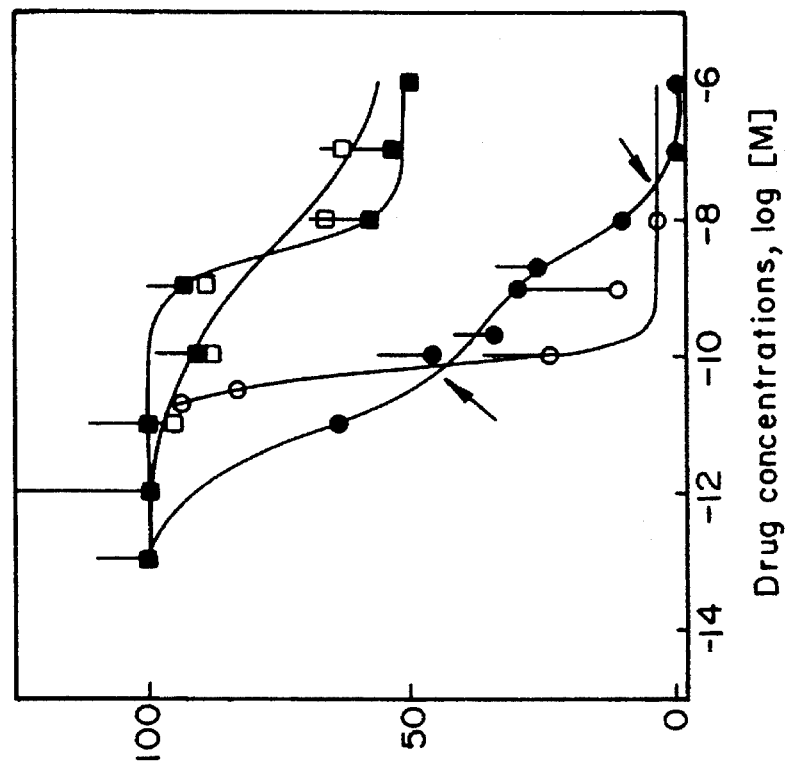

Limited modifications at the N-acyl group of the lateral chain (e.g. cyclopropyl substitution alone) affected the biological activity (4j, see Table IV), and this effect could be counteracted by only few concomitant substitutions at $C_2$ of the indole nucleus (R), that were able also to counteract to a great extent the loss of the affinity: halogenation and methylation (4c,h,m). Most importantly, one of these new agonists unexpectedly labeled a different subtype (isoform) of the melatonin receptor, as seen from the observed biphasic inhibition curves and the differences in the affinity values with the melatonin receptor in the suprachiasmatic nuclei (FIG. 2). The significance of the test is that increasing doses of an analog, incubated together with the radiolabeled ligand will compete with the radiolabeled ligand for the limited number of binding sites available, and will produce a single-phase inhibition curve, when a single receptor type is present (e.g. in pituitary parts tuberalis) or biphasic inhibition curves, when a second receptor type with different affinity is also present in the cells (e.g. in the suprachiasmatic nuclei). The differences can be revealed by increasing the washing time following incubation, under in vitro autoradiography procedure, thus creating conditions for dissociation of the lower-affinity receptor type. Clearly, two receptor forms with two different affinity constants, are present in the suprachiasmatic nuclei, contrary to the single type of lower affinity present in pituitary pars tuberalis. This phenomenon is very evident when using 2-bromo-N-cyclopropanoyl-5-methoxytryptamine (4h) in the competition experiments (FIG. 2A, Table VI). Thus, 2-bromo-N-cyclopropanoyl-5-methoxytryptamine emerge as a selective melatonin receptor agonist, binding with extremely high affinity for the predominant melatonin receptor class present in the SCN.

TABLE VI

Competitive potencies (Ki, in nM) values of the tested compounds against radioactive 2-[$^{125}$I]-labeled melatonin, under in vitro quantitative autoradiography binding conditions with melatonin receptors, determined in parallel in the suprachiasmatic nuclei (SCN) and pars tuberalis (PT) of the same animals (rats), from three independent experiments.

| Drug | SCN | PT |
|---|---|---|
| 2-Phenylmelatonin (4d) | 0.008 | 0.49 |
| 2-Bromomelatonin (4k) | 0.074 | 0.20 |
| 2-Iodomelatonin | 0.023 | 0.38 |
| 2-Methylmelatonin (4a) | 0.050 | 1.00 |
| N-cyclopropanoyl-5-methoxytryptamine (4j) | 0.005 | 0.16 |
| **2-Bromo-N-cyclopropanoyl-5-methoxytryptamine (4h) | *0.0025[a]* *1.350* | 0.20 |
| 2-Phenyl-N-cyclopropanoyl-5-methoxytryptamine (4g) | 0.039 | 0.50 |
| Melatonin | 0.120 | 2.4 |
| N-acetylserotonin | 245 | 292 |
| The rest of the hydroxyindoles, indoles and miscellaneous neurotransmitters (as listed in Table I) | >100,000 | >100,000 |

**The compound labels two receptor subtypes, only in the SCN, one[a] with extremely high affinity (≈60 times higher than melatonin and ≈10 times higher than 2-iodomelatonin). Both values are given in italics. Note the differences between the SCN and PT, in terms of the affinity values and order of potencies of all compounds.

Clearly, the pharmacological profile (competitive potencies of the tested compounds) in the SCN is very different, strongly suggesting the existence of a different receptor type, binding with an extremely high affinity 2-bromo-N-cyclopropanoyl-5-methoxytryptamine; see also the differences in the inhibition curves in FIG. 1. Therefore, 2-Bromo-N-cyclopropanoyl-5 -methoxytryptamine behaves as a selective melatonin agonist in the SCN, the site of the biological circadian clock (see also biological activity data in Table IV).

The unexpected discovery of this new receptor subtype in the circadian biological clock gives for the first time the possibility of using selective melatonin agonists for treatment of circadian rhythm disorders.

Subsequently, the efforts concentrated on creation of methods and pharmaceutical compositions for transdermal application that would allow the active compound(s) to achieve sustained peripheral blood levels for a period of 6–8 hours.

As pointed out, oral administration of melatonin leads to a rapid absorption, high plasma levels and rapid bioavailability deterioration, due to the very short elimination half-life of melatonin. This is in contrast to the physiological situation, where endogenous melatonin is continuously available for 6–8 h. (see FIG. 3). Long (6–8 h) duration of the endogenous melatonin peak is a fundamental biological feature necessary for the functionality of the melatoninergic system. Transdermal (transcutaneous) administration of melatonin or its agonists, leads to a continuous bioavailability of the compound in the peripheral blood plasma, thus successfully mimicking the natural conditions (FIG. 4, 5). Therefore, a significant advantage is achieved over oral route of administration.

The peripheral plasma elimination half-life of melatonin is short (≈27 min). The peripheral plasma half-lives of 2-halogenated melatonins, and 2-halogenated-N-acetyl-5-methoxytryptamines, and 2-halogenated-N-cyclopropanoyl-5-methoxytryptamines is much longer, and present advantage over melatonin (See Table VII). The significance of the test is in that by treating experimental animals and obtaining blood samples at determined periods of time following administration, the bioavailability of a compound (directly proportional to the elimination half-life) can be estimated. In the example given in Table VII, clearly, both 2-iodomelatonin and 2-bromomelatonin express about two times higher bioavailability values than melatonin (T½ elimination for melatonin=27.06 min; T½ elimination for 2-iodomelatonin= 61.75 min; T½ elimination for 2-bromomelatonin=68.43 min). The bioavailability of 2-bromo-N-cyclopropanoyl-5-methoxytryptamine is even longer (T½ elimination=72.62 min).

TABLE VII

Pharmacokinetic parameters of melatonin, 2-iodomelatonin, 2-bromomelatonin and 2-bromo-N-cyclopropanoyl-5-methoxytryptamine in the peripheral blood after a single dose of 30 mg given intraperitoneally to rats.

| Drug | T½elimination (min) | T½absorption (min) | Cmax (mg/L) | Tmax (min) |
|---|---|---|---|---|
| Melatonin | 27.06 | 8.61 | 19.71 | 30 |
| 2-IM | 61.75* | 5.65 | 12.37 | 20 |
| 2-BM | 68.43* | 6.24 | 13.43 | 22 |
| 2-Br—N-cM | 72.62* | 7.11 | 11.21 | 25 |

*p < 0.001 vs melatonin. Abbreviations: T½elimination, elimination half-life; T½absorption, absorption rate; Cmax, peak concentration; Tmax, time to peak concentration; 2-IM, 2-iodomelatonin; 2-BM, 2-bromomelatonin; 2-Br—N-cM, 2-bromo-N-cyclopropanoyl-5-methoxytryptamine.

The data reported in the Tables and shown in the Figures clearly demonstrate that the affinities of some of the new 2- and 2-substituted N-acyl-5-methoxytryptamines, such as 2-bromomelatonin, 2,6-dibromomelatonin, 2-bromo-N-cyclopropanoyl-5-methoxytryptamine, and 2-bromo-N-cyclopropanoyl-5-methoxytryptamine for the melatonin receptor, the longer elimination half-lives and their enhanced biological activities represent an unexpected result. Moreover, 2-bromo-N-cyclopropanoyl-5-methoxytryptamirte binds with extremely high affinity to the melatonin receptor isoform present in the SCN, the site of the circadian clock. These melatonin agonists present indisputable advantages over melatonin for treatment of circadian rhythms disorders. It is well known that the duration of the melatonin peak is the fundamental signal for the circadian clock. Melatonin must be continuously available for a period of 6–8 hours during the subjective night, in order to properly convey the circadian and photoperiodic information. Methods and pharmaceutical compositions that would allow for continuous, controlled release of melatonin and its selective agonists have not been disclosed before. The transdermal methods of application and the pharmaceutical compositions clearly present a major advantage over the oral or intravenous administration, in that physiological levels and a two- to three times longer bioavailability of the administered compounds is achieved.

FIG. 1A and FIG. 1B. Examples of the effects of an agonist (4a, hatched bar, $1E^{-6}M$ concentration in the electrode) applied by iontophoresis, on the spontaneous firing activity of single cortical neurons in the rabbit parietal cortex. Triangles denote the beginning of the application of phaclofen and bicuculline ($1E^{-4}M$ and $5E^{-4}M$, corresponding concentrations in the electrodes). The arrow denotes the beginning of administration of the antagonist (4d, $1E^{-6}M$ concentration in the electrode) FIG. B. Note that the prolonged firing rate inhibition, induced by 4a, FIG. 1A is completely blocked by preceding co-administration of 4d (FIG. 1B.)

FIG. 2A and FIG. B. Autoradiographic analysis: effect of short washes (after incubation) on [$^{125}$I]-labeled melatonin binding in presence of varying concentrations of 2-iodomelatonin (open squares, 2 minutes wash; open circles, 10 minutes wash) and 2-bromo-N-cyclopropanoyl-5-methoxytryptamine (closed squares, 2 minutes wash; closed circles, 10 minutes wash) in the rat suprachiasmatic nuclei (panel A) and pars tuberalis (panel B). The arrows denote the two points of saturation of the biphasic 2-bromo-N-cyclopropanoyl-5-methoxytryptamine curve, indicating the existence of two receptor types. Note the difference (all monophasic curves, independent of the wash time) in the pars tuberalis. Clearly, 2-bromo-N-cyclopropanoyl-5-methoxytryptamine labels two receptor subtypes with two different affinities: 0.0025 nM and 1.35 nM in the suprachiasmatic nuclei, vs a single site with an affinity of 0.196 nM in the pars tuberalis. In that tissue (suprachiasmatic nuclei), 2-bromo-N-cyclopropanoyl- 5-methoxytryptamine exhibits and affinity for the melatonin receptor (isoform) about 60 times higher than melatonin and 10 times higher than 2-iodomelatonin.

Figure 3:
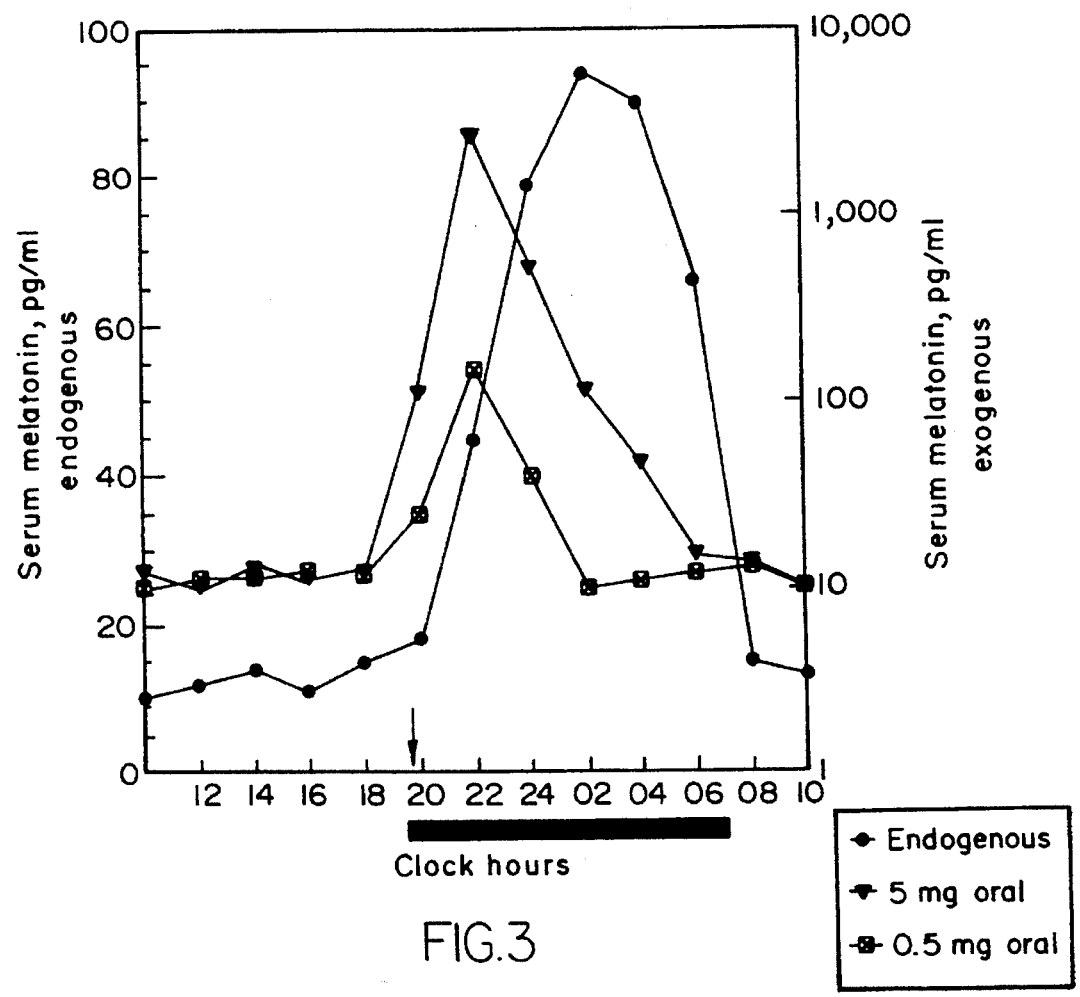
FIG. 3 is a plot of the endogenous serum melatonin levels with time, in comparison to the serum levels achieved following oral melatonin administration of 5 mg and 0.5 mg melatonin. The black horizontal bar denotes the nighttime. Note the logarithmic scale for the melatonin levels achieved following exogenous administration.
Figure 4:
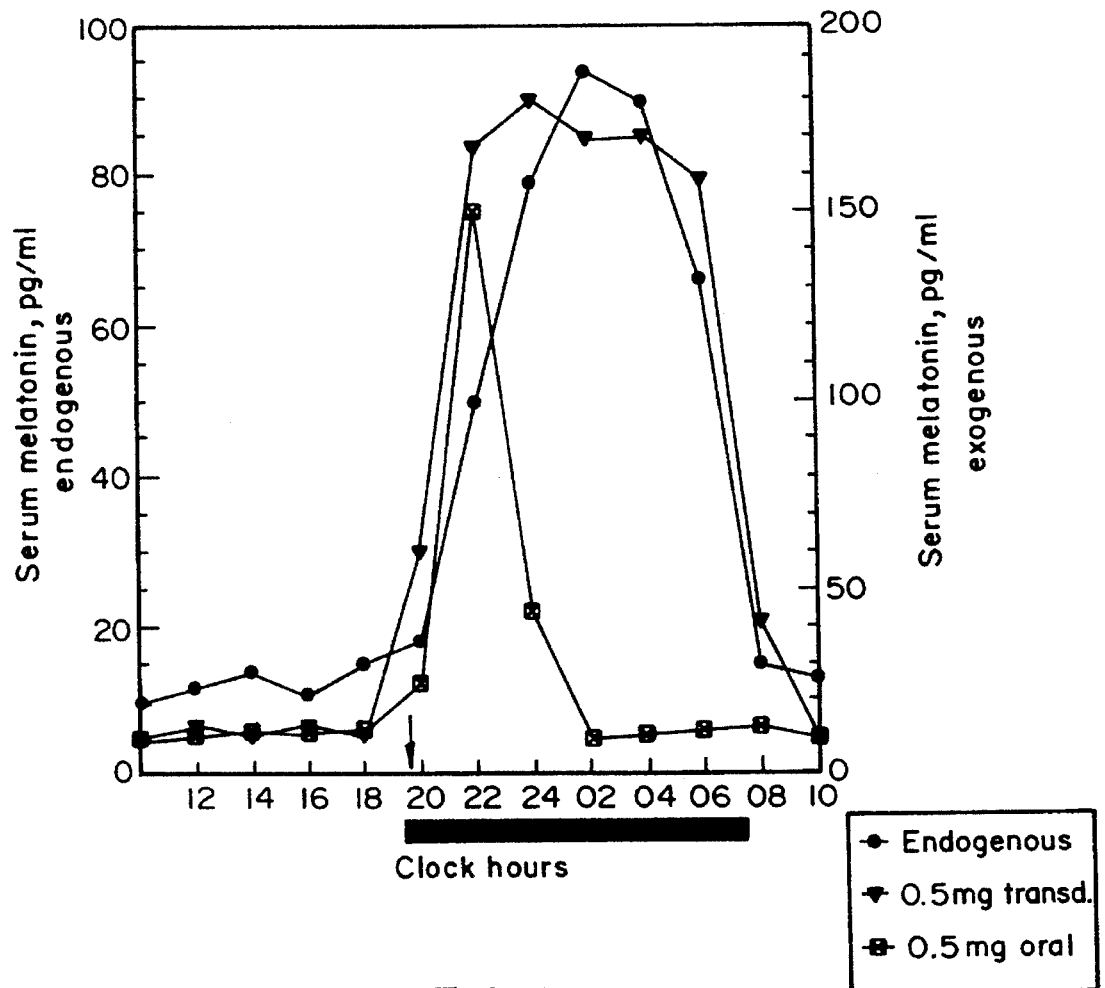
FIG. 4 shows that the peripheral blood melatonin levels following transdermal administration of melatonin in a low dose of 0.5 mg essentially mimics the endogenous melatonin peak, as opposed to oral administration of the same dose.

FIG. 3. Peripheral melatonin blood levels in healthy volunteers (n=8/group) given 5 mg or 0.5 mg melatonin orally at 19:45 h (arrow), compared to the endogenous melatonin blood levels at nighttime in the same subjects (n=16) examined 24 hours before taking melatonin. Black bar denotes the scotophase. During the night when melatonin was given, the subjects were exposed to bright light, to suppress the endogenous melatonin peak. Note that melatonin given orally results in a sharp increase in the peripheral blood levels, that does not correspond to the endogenous melatonin pattern. Five mg oral melatonin produces peripheral blood levels that are about 30 times higher than the physiological ones: note the logarithmic scale for the melatonin levels achieved following oral administration. On the other hand, 0.5 mg melatonin given orally results in peripheral blood levels that are abnormally short. They are comparable to the physiological levels for only 2 hours. Note that the endogenous melatonin peak lasts 6–8 hours.

FIG. 4. Peripheral melatonin blood levels in healthy volunteers (n=8/group) given 0.5 mg melatonin orally at 19:45 h or 0.5 mg melatonin, at the same time (arrow), using transdermal application in gel (Gel 1, see examples), compared to the endogenous melatonin blood levels at nighttime in the same subjects (n=16), examined 24 hours before taking melatonin. Black bar denotes the scotophase. During the treatment night, the subjects were exposed to bright light, to suppress the endogenous melatonin peak. Note that oral melatonin administration results in a sharp increase in the peripheral blood levels, followed by a rapid decline, that does not correspond to the endogenous melatonin pattern, while the same dose applied by a transdermal gel results in peripheral blood levels that very closely mimic the endogenous melatonin pattern (physiologically adequate melatonin levels are present in the peripheral blood for about eight hours, until the removal of the gel [arrowhead]). Note the double scale for the melatonin levels achieved following exogenous administration.

Figure 5:
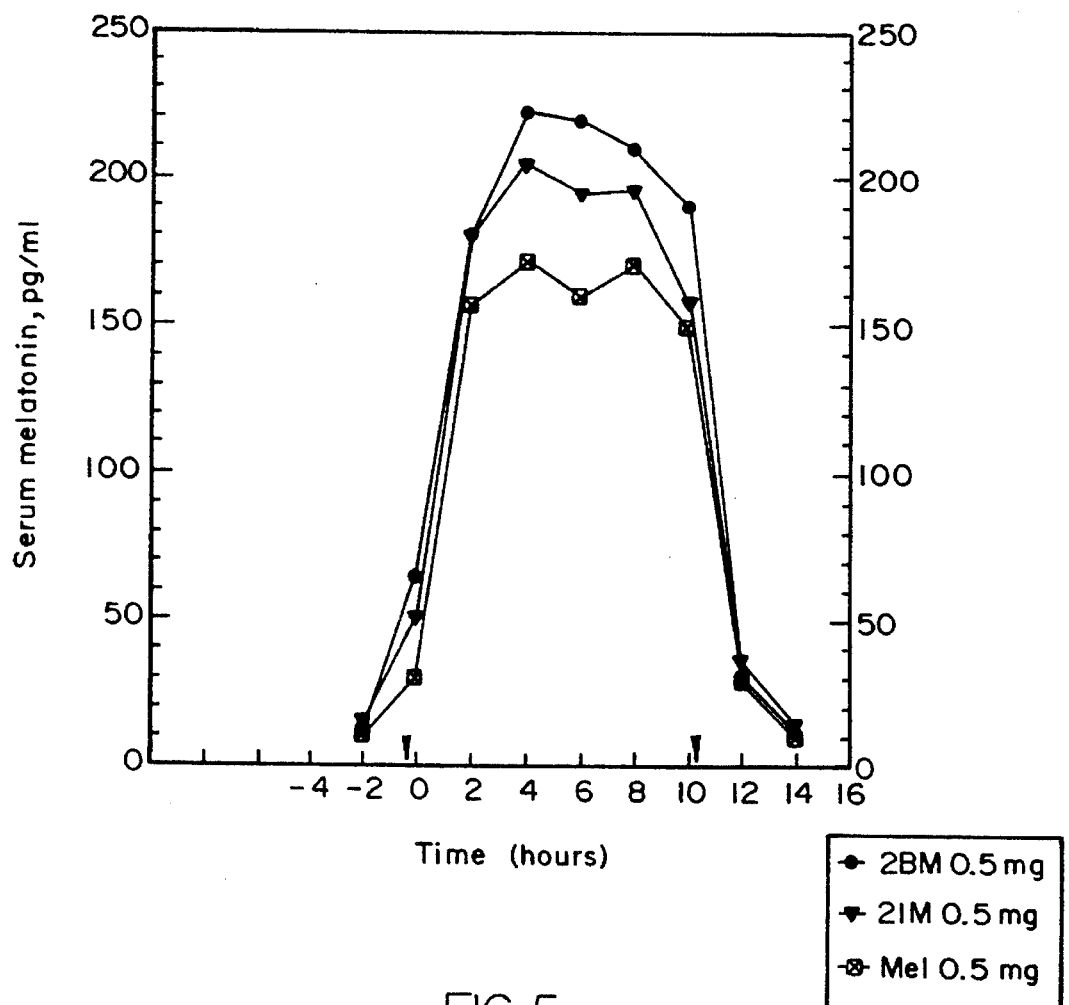
FIG. 5 shows that the melatonin agonists 2-bromomelatonin and 2-iodomelatonin applied transdermally in a dose of 0.5 mg show similar, but increased bioavailability in the peripheral blood.

FIG. 5. Peripheral blood melatonin, 2-iodomelatonin (2IM) and 2-bromomelatonin (2BM) levels following transdermal application with gel (Gel 2, see examples) in healthy human volunteers (n=8/group), during daytime. Arrowheads indicate the application and the removal of the gel. Note that physiologically adequate levels are achieved for the whole period, closely mimicking an endogenous melatonin peak. 2IM and 2BM show significantly better transdermal penetration and bioavailability, with the same dose (0.5 mag) applied. Time zero denotes the first sample following gel application.

Examples (all quantities are reported in grams): Note: The names of all complex compounds listed below are CTFA* -adopted names.
*US Chemical Toilet and Fragrance Association

| GEL 1 | |
|---|---|
| Carbomer 940 | 4 |
| Carbomer 1238 | 4 |
| Ethyl Alcohol | 50 |
| Melatonin | 1 |
| Imidazolidinyl Urea | 3 |
| Glycerin | 20 |
| Tea | 10 |
| PEG-40 Hydrogenated Castor Oil | 2 |
| Cyclomethicone | 1 |
| Alkyl Benzoate | 1 |
| Isodamascon | 0.3 |
| Deionized water | to 1000 |

In this example 1 g melatonin can be substituted with 0.3 g 2-bromomelatonin, or 0.3 g 2-iodomelatonin, or 0.3 g 2,6-dibromomelatonin, or 0.2 g 2-bromo-N-cyclopropanoyl-5-methoxytryptamine.

| GEL 2 | |
|---|---|
| Carbomer 940 | 4 |
| Carbomer 1238 | 4 |
| Ethyl Alcohol | 320 |
| Melatonin | 10 |
| Imidazolidinyl Urea | 3 |
| Glycerin | 20 |
| Tea | 10 |
| PEG-40 Hydrogenated Castor Oil | 2 |
| Cyclomethicone | 1 |
| Alkyl Benzoate | 1 |
| Isodamascon | 0.3 |
| Deionized water | to 1000 |

In this example 10 g melatonin can be substituted with 3 g 2-bromomelatonin, or 3 g 2-iodomelatonin, or 3 g 2,6-dibromomelatonin, or 2 g 2-bromo-N-cyclopropanoyl-5-methoxytryptamine.

| GEL 3 | |
|---|---|
| Carbomer 940 | 4 |
| Carbomer 1238 | 4 |
| Ethyl Alcohol | 303 |
| Melatonin | 30.3 |
| Phospholipids | 91 |
| Imidazolidinyl Urea | 3 |
| Glycerin | 20 |
| Tea | 10 |
| PEG-40 Hydrogenated Castor Oil | 2 |
| Cyclomethicone | 1 |
| Alkyl Benzoate | 1 |
| Isodamascon | 0.3 |
| Deionized water | to 1000 |

In this example 30.3 g melatonin can be substituted with 9 g 2-bromomelatonin, or 9 g 2-iodomelatonin, or 9 g 2,6-dibromomelatonin, or 6 g 2-bromo-N-cyclopropanoyl-5-methoxytryptamine.

| GEL 4 | |
|---|---|
| Polyglyceryl Methacrilate | 350 |
| Ethyl Alcohol | 50 |
| Melatonin | 1 |
| PEG-40 Hydrogenated Castor Oil | 5 |
| Phenoxyethanol | 2 |
| Imidazolidinyl Urea | 3 |
| Deionized water | to 1000 |

In this example 1 g melatonin can be substituted with 0.3 g 2-bromomelatonin, or 0.3 g 2-iodomelatonin, or 0.3 g 2,6-dibromomelatonin, or 0.2 g 2-bromo-N-cyclopropanoyl-5-methoxytryptamine.

| OIL 1 | |
|---|---|
| Cyclomethicone | 478 |
| Dimethicone | 250 |
| Isostearyl palmitate | 250 |
| Tocopheryl Acetate | 20 |
| Melatonin | 1 |
| 2-Phenoxyethanol | 2 |

In this example 1 g melatonin can be substituted with 0.3 g 2-bromomelatonin, or 0.3 g 2-iodomelatonin or 0.3 g 2,6-dibromomelatonin, or 0.2 g 2-bromo-N-cyclopropanoyl-5-methoxytryptamine.

| EMULSION Oil/Water | |
|---|---|
| PEG-8 Alkyl Ester | 100 |
| Cetearyl Alcohol | 15 |
| Glyceryl Triisostearate | 30 |
| Hydrogenated Tollow Glycerides | 5 |
| Alkyl Benzoate | 70 |
| Jojoba Oil | 15 |
| Melatonin | 1 |
| Dimethicone | 10 |
| Tocopheryl Acetate | 10 |
| Magnesium Ascorbyl Phosphate | 5 |
| Glycerin | 30 |
| Phenoxyethanol | 2 |
| Imidazolidinyl Urea | 3 |
| Deionized water | to 1000. |

In this example 1 g melatonin can be substituted with 0.3 g 2-bromomelatonin, or 0.3 g 2-iodomelatonin or 0.3 g 2,6-dibromomelatonin, or 0.2 g 2-bromo-N-cyclopropanoyl-5-methoxytryptamine.

| EMULSION Water/Silicone-oil 1 | |
| --- | --- |
| Lauryl Methicone Copolyol | 20 |
| Dimethicone | 100 |
| Cyclomethicone | 50 |
| Melatonin | 10 |
| Tocopheryl Acetate | 2 |
| Alkyl Lactate | 47 |
| PPG-3 Miristate | 5 |
| Sodium Chloride | 20 |
| Glycerin | 20 |
| Imidazolidinyl Urea | 2 |
| Deionized water | to 1000 |

In this example 10 g melatonin can be substituted with 3 g 2-bromomelatonin, or 3 g 2-iodomelatonin, or 3 g 2,6-dibromomelatonin or 2 g 2-bromo-N-cyclopropanoyl-5-methoxytryptamine.

| EMULSION Water/Silicone-oil 2 | |
| --- | --- |
| Cetyl Dimethicone Copolyol | 50 |
| Cetyl Dimethicone and Polyglyceryl-3 Oleate and Hexyl Laurate Polyisoprene (mix) | 140 |
| Dimethicone | 20 |
| Cyclomethicone | 30 |
| Tocopheryl Acetate | 1 |
| Melatonin | 1 |
| Sodium Chloride | 20 |
| Phenoxyethanol | 2 |
| Imidazolidinyl Urea | 3 |
| Sorbitol | 20 |
| Deionized water | to 1000 |

In this example 1 g melatonin can be substituted with 0.3 g 2-bromomelatonin, or 0.3 g 2-iodomelatonin or 0.3 g 2,6-dibromomelatonin, or 0.2 g 2-bromo-N-cyclopropanoyl-5-methoxytryptamine.

The trade names of the compounds used in the examples are CTFA-accepted names and the chemical compositions and the producers are as follows:

Carbomer 940 and Carbomer 1248 (Goodrich, USA) are homopolymers of acrylic acid, crosslinked with alkyl ether of pentaerytritol or alkyl ether of sucrose, respectively.

Cyclomethicone (Dow Corning) is a cyclic polydimethylsiloxane compound (3–6 units).

PEG-40 Hydrogenated Castor Oil (BASF, Germany) is a polyethylene glycol derivative of Hydrogenated Castor Oil with an average of 40 moles of ethylene oxide.

PEG-8 Alkyl Esters (Vevi, Italy) is polyethylene glycol (8 units) ester of synthetic saturated acids, containing 12–20 carbon atoms in the alkyl chain.

Isodamascon (Dragoco, Germany) is trans-2-butanone, 1-(2,4,4-trimethyl-1 and 2-cyclohexanyl).

Lauryl Methicone Copolyol (Dow Corning, USA) is the polymer of monomethyl polysiloxane with lauryl side chains and polyoxyethylene and/or polyoxypropylene end chains.

Cetyl Dimethicone Copolyol (Goldschmidt, Germany) is a copolymer of Cetyl Dimethicone and Dimethicone Copolyol (copolymer of dimethylsiloxane, cetylmethylsiloxane polymer and polymer of dimethylsiloxane with polyoxyethylene and polyoxypropylene side chains.

Cetyl Dimethicone and Polyglyceryl-3 Oleate and Hexyl Laureate (Goldschmidt, Germany) is dimethylsiloxane cetylmethylsiloxane polymer and ester of oleic acid with dimer of glycerin and ester of hexyl alcohol with lauric acid.

Polyisoprene (BBF, Germany) is the polymer of isoprene.

Dimethicone (Goldschmidt, Germany) is a mixture of fully methylated linear silicone polymer, blocked with trimethylsiloxy unit.

In all mentioned above excipients melatonin or its agonists may be included together with one of the following carriers:

1. Phospholipids of liposomic structure, niosomic and non-niosomic structure.
2. Solubilizing agents
3. Bovine kappa elastin
4. Proteins or peptides Melatonin and/or its agonists, as mentioned in the examples above may be combined with penetration-delaying agents, such as proteic microspheres or cellulose, or other materials, according to the therapeutic necessities.

What is claimed is:

1. A compound having the ability to combat chronopathology of jet lag or delayed sleep phase syndrome of the formula:

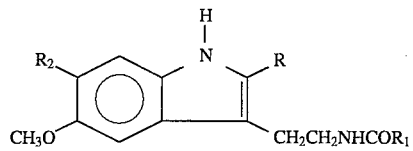

wherein a) R=isopropyl $R_1$=$CH_3$ $R_2$=H b) R=cyclohexyl $R_1$=$CH_3$ $R_2$=H c) R=methyl $R_1$=cyclopropyl $R_2$=H d) R=phenyl $R_1$=cyclopropyl $R_2$=H e) R=Br $R_1$=cyclopropyl $R_2$=H f) R=Br $R_1$=$CH_3$ $R_2$=Br (g) R=I $R_1$=cyclopropyl $R_2$=H or (h) R=Br $R_1$=$CH_3$ $R_2$=H.

2. A method of treatment of a living subject affected by chronopathology of jet lag or delayed sleep phase syndrome, which consists of administering by the transdermal route to said living subject a composition containing as the active ingredient 0.1–5% of a compound which is a member selected from the group consisting of melatonin, 2-methylmelatonin, 2-bromomelatonin, 2-iodomelatonin, 2,6-dibromomelatonin, 2-cyclohexylmelatonin, 2-bromo-N-cyclopropanoyl-5-methoxytryptamine, and 2-iodo-N-cyclopropanoyl-5-methoxytryptamine.

3. The method according to claim 2, wherein said composition contains 2-bromo-N-cyclopropanoyl-5-methoxytryptamine, as an extremely high-affinity selective agonist for the melatonin receptor isoform in the suprachiasmatic nuclei.

4. The method according to claim 2 wherein said composition is in form of an oil, a gel, a paste, a cream or an emulsion.

5. The method according to claim 2 wherein said composition is applied on a solid support which is a patch, occluded or non-occluded gauze.

6. The method according to claim 2, wherein said composition additionally comprises a penetration retardant.

7. The method according to claim 6, wherein said penetration retardants are proteic microspheres or cellulose.

8. A pharmaceutical composition in the form of a gel, a paste, a cream or an emulsion for transdermal administration which contains as the active component melatonin or a melatonin agonist of formula:

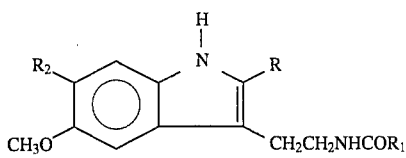

wherein:

R is cyclohexyl, CH$_3$, Br, I, or H

R$_1$ is CH$_3$ or cyclopropyl and

R$_2$ is H or Br, in the amount of 0.1–5% of the total composition and pharmaceutically acceptable carriers and excipients.

9. A pharmaceutical composition according to claim 8 in the form of a gel which consists of:

| Carbomer 940 | 4 grams |
|---|---|
| Carbomer 1238 | 4 grams |
| Ethyl Alcohol | 50 grams |
| Imidazolidinyl Urea | 3 grams |
| Glycerin | 20 grams |
| Tea | 10 grams |
| PEG-40 Hydrogenated Castor Oil | 2 grams |
| Cyclomethicone | 1 grams |
| Alkyl Benzoate | 1 grams |
| Isodamascon | 0.3 grams | and a member selected from the group consisting of

Melatonin, in the amount of 1 gram, 0.3 g 2-bromomelatonin, 0.3 g 2-iodomelatonin, 0.3 g 2,6-dibromomelatonin, 0.3 g 2-methylmelatonin, 0.2 g 2-bromo-N-cyclopropanoyl-5-methoxytryptamine and 0.2 g 2-iodo-N-cyclopropanoyl-5-methoxytryptamine and Deionized water to 1000 grams.

10. A pharmaceutical composition according to claim 8, in the form of a gel which consists of:

| Carbomer 940 | 4 grams |
|---|---|
| Carbomer 1238 | 4 grams |
| Ethyl Alcohol | 320 grams |
| Imidazolidinyl Urea | 3 grams |
| Glycerin | 20 grams |
| Tea | 10 grams |
| PEG-40 Hydrogenated Castor Oil | 2 grams |
| Cyclomethicone | 1 grams |
| Alkyl Benzoate | 1 grams |
| Isodamascon | 0.3 grams | and a member selected from the group consisting of

Melatonin in the amount of 10 grams, 3 g 2-bromomelatonin, 3 g 2-iodomelatonin, 3 g 2-methylamelatonin, 3 g 2,6-dibromomelatonin, 2 g 2-bromo-N-cyclopropanoyl-5-methoxytryptamine and 2 g 2-iodo-N-cyclopropanoyl-5-methoxytryptamine and Deionized water to 1000 grams.

11. A pharmaceutical composition according to claim 8, in the form of a gel which consists of:

| Carbomer 940 | 4 grams |
|---|---|
| Carbomer 1238 | 4 grams |
| Ethyl Alcohol | 303 grams |
| Phospholipids | 91 grams |
| Imidazolidinyl Urea | 3 grams |
| Glycerin | 20 grams |
| Tea | 10 grams |
| PEG-40 Hydrogenated Castor Oil | 2 grams |
| Cyclomethicone | 1 grams |
| Alkyl Benzoate | 1 grams |
| Isodamascon | 0.3 grams | and a member selected from the group consisting of

Melatonin in the amount of 30.3 grams, 9 g 2-bromomelatonin, 9 g 2-iodomelatonin, 9 g 2-methylmelatonin, 9 g 2,6-dibromomelatonin, 6 g 2-bromo-N-cyclopropanoyl-5-methoxytryptamine and 6 g 2-iodo-N-cyclopropanoyl-5-methoxytryptamine and Deionized water to 1000 grams.

12. A pharmaceutical composition according to claim 8, in the form of a gel which consists of:

| Polyglyceryl Methacrylate | 350 grams |
|---|---|
| Ethyl Alcohol | 50 grams |
| PEG-40 Hydrogenated Castor Oil | 5 grams |
| Phenoxyethanol | 2 grams |
| Imidazolidinyl Urea | 3 grams | and a member selected from the group consisting of

Melatonin in the amount of 1 g, 0.3 g 2-bromomelatonin, 0.3 g 2-iodomelatonin, 0.3 g 2-methylmelatonin, 0.3 g 2,6-dibromomelatonin, 0.2 g 2-bromo-N-cyclopropanoyl-5-methoxytryptamine and 0.2 g 2-iodo-N-cyclopropanoyl-5-methoxytryptamine and Deionized water to 1000 grams.

13. A pharmaceutical composition according to claim 8, in the form of an oil which consists of:

| Cyclomethicone | 478 grams |
|---|---|
| Dimethicone | 250 grams |
| Isostearyl palmitate | 250 grams |
| Tocopheryl Acetate | 20 grams |
| 2-Phenoxyethanol | 2 grams | and a member selected from the group consisting of

Melatonin in the amount of 1 gram, 0.3 g 2-bromomelatonin, 0.3 g 2-iodomelatonin, 0.3 g 2-methylmelatonin, 0.3 g 2,6-dibromomelatonin, 0.2 g 2-bromo-N-cyclopropanoyl-5-methoxytryptamine and 0.2 g 2-iodo-N-cyclopropanoyl-5-methoxytryptamine.

14. A pharmaceutical composition according to claim 8, in the form of an emulsion of oil/water which consists of:

| PEG-8 Alkyl Ester | 100 grams |
|---|---|
| Cetearyl Alcohol | 15 grams |
| Glyceryl Triisostearate | 30 grams |
| Hydrogenated Tallow Glycerides | 5 grams |
| Alkyl Benzoate | 70 grams |
| Jojoba Oil | 15 grams |
| Dimethicone | 10 grams |
| Tocopheryl Acetate | 10 grams |
| Magnesium Ascorbyl Phosphate | 5 grams |
| Glycerin | 30 grams |
| Phenoxyethanol | 2 grams |
| Imidazolidinyl Urea | 3 grams | and a member selected from the group consisting of

Melatonin in the amount of 1 gram, 0.3 g 2-bromomelatonin, 0.3 g 2-iodomelatonin, 0.3 g 2-methylmelatonin, 0.3 g 2,6-dibromomelatonin, 0.2 g 2-bromo-N-cyclopropanoyl-5-methoxytryptamine and 0.2 g 2-iodo-N- cyclopropanoyl-5-methoxytryptamine and Deionized water to 1000 grams.

15. A pharmaceutical composition according to claim 8, in the form of an emulsion which consists of:

| | |
|---|---|
| Lauryl Methicone Copolyol | 20 grams |
| Dimethicone | 100 grams |
| Cyclomethicone | 50 grams |
| Tocopheryl Acetate | 2 grams |
| Alkyl Lactate | 47 grams |
| PPG-3 Miristate | 5 grams |
| Sodium Chloride | 20 grams |
| Glycerin | 20 grams |
| Imidazolidinyl Urea | 2 grams | and a member selected from the group consisting of

Melatonin in the amount of 10 grams, 3 g 2-bromomelatonin, 3 g 2-iodomelatonin, 3 g 2-methylmelatonin, 3 g 2,6-dibromomelatonin, 2 g 2-bromo-N-cyclopropanoyl-5-methoxytryptamine and 2 g 2-iodo-N-cyclopropanoyl-5-methoxytryptamine and Deionized water to 1000 grams.

16. A pharmaceutical composition according to claim 8, in the form of an emulsion which consists of:

| | |
|---|---|
| Cetyl Dimethicone Copolyol | 50 grams |
| Cetyl Dimethicone and Polyglycerol-3 Oleate and Hexyl Laurate Polyisoprene (mix) | 140 grams |
| Dimethicone | 20 grams |
| Cyclomethicone | 30 grams |
| Tocopheryl Acetate | 1 grams |
| Sodium Chloride | 20 grams |
| Phenoxyethanol | 2 grams |
| Imidazolidinyl Urea | 3 grams |
| Sorbitol | 20 grams | and a member selected from the group consisting of

Melatonin in the amount of 1 gram, 0.3 g 2-bromomelatonin, 0.3 g 2-iodomelatonin, 0.3 g 2-methylmelatonin, 0.3 g 2,6-dibromomelatonin, 0.2 g 2-bromo-N-cyclopropanoyl-5-methoxytryptamine and 0.2 g 2-iodo-N-cyclopropanoyl-5-methoxytryptamine and Deionized water to 1000 grams.

17. A method of treatment of a living subject to achieve sustained peripheral blood levels for a period of 6–8 hours which consists of administering by the transdermal route to said living subject a composition containing as the active ingredient 0.1–5% of a compound which is a member selected from the group consisting of melatonin, 2-methylmelatonin, 2-bromomelatonin, 2-iodomelatonin, 2,6-dibromomelatonin, 2-cyclohexylmelatonin, 2-bromo-N-cyclopropanoyl-5-methoxytryptamine and 2-iodo-N-cyclopropanoyl-5-methoxytryptamine.

18. The method according to claim 17 wherein said composition contains 2-bromo-N-cyclopropanoyl-5-methoxytryptamine, as an extremely high-affinity selective agonist for the melatonin receptor isoform in the suprachiasmatic nuclei.

19. The method according to claim 17 wherein said composition is in form of an oil, a gel, a paste, a cream or an emulsion.

20. The method according to claim 17 wherein said composition is applied on a solid support which is a patch, occluded or non-occluded gauze.

21. The method according to claim 17, wherein said composition additionally comprises a penetration retardant.

22. The method according to claim 17, wherein said penetration retardants are proteic microspheres or cellulose.

* * * * *

UNITED STATES PATENT AND TRADEMARK OFFICE
CERTIFICATE OF CORRECTION

PATENT NO. : 5,552,428

DATED : September 3, 1996

INVENTOR(S) : FRASCHINI et al

It is certified that error appears in the above-identified patent and that said Letters Patent is hereby corrected as shown below:

On the title page, item
   [73]  Assignee:    Instituto Farmacologico Lombardo-IFLO, S.a.S.
                          Milan, Italy (Part Interest)

Signed and Sealed this

Fourth Day of February, 1997

*Attest:*

BRUCE LEHMAN

*Attesting Officer*        *Commissioner of Patents and Trademarks*